US009510900B2

(12) United States Patent
Abou-Marie et al.

(10) Patent No.: US 9,510,900 B2
(45) Date of Patent: Dec. 6, 2016

(54) ELECTROSURGICAL DEVICE FOR CREATING A CHANNEL THROUGH A REGION OF TISSUE AND METHODS OF USE THEREOF

(75) Inventors: Rund Abou-Marie, Mississauga (CA); Taras Juzkiw, Mississauga (CA); Gareth Davies, Toronto (CA); Maria Luk, Toronto (CA); Ramsey Leung, Toronto (CA); Mark Mosley, Toronto (CA); Christine Wong, Toronto (CA); Kelly Albert, Brampton (CA)

(73) Assignee: BAYLIS MEDICAL COMPANY INC., Montreal (CA)

( * ) Notice: Subject to any disclaimer, the term of this patent is extended or adjusted under 35 U.S.C. 154(b) by 516 days.

(21) Appl. No.: 12/926,292

(22) Filed: Nov. 8, 2010

(65) Prior Publication Data

US 2011/0118735 A1 May 19, 2011

Related U.S. Application Data

(63) Continuation-in-part of application No. 11/520,754, filed on Sep. 14, 2006, now Pat. No. 7,828,796, which is a continuation-in-part of application No. 11/265,304, filed on Nov. 3, 2005, now Pat. No.

(Continued)

(51) Int. Cl.
*A61B 18/14* (2006.01)
*A61B 18/00* (2006.01)
(Continued)

(52) U.S. Cl.
CPC ............ *A61B 18/1492* (2013.01); *A61B 90/39* (2016.02); *A61B 2017/00867* (2013.01); *A61B 2018/0041* (2013.01); *A61B 2018/00083* (2013.01); *A61B 2018/00101* (2013.01);

(Continued)

(58) Field of Classification Search
CPC ................ A61B 2018/1417; A61B 2018/142; A61B 18/1492; A61B 2018/00101; A61B 2018/00089; A61B 2018/00095
USPC .............................................. 606/45, 39, 46
See application file for complete search history.

(56) References Cited

U.S. PATENT DOCUMENTS 4,669,467 A * 6/1987 Willett et al. ..................... 606/7
4,832,048 A * 5/1989 Cohen ............................ 606/41

(Continued)

OTHER PUBLICATIONS

J. E Della, "Non-Final rejection in the case of U.S. Appl. No. 11/520,754",Aug. 19, 2009.

(Continued)

*Primary Examiner* — Jaymi Della

(57) ABSTRACT

An electrosurgical device and methods are disclosed for creating a channel through a region of tissue. The device comprises an elongate member for receiving the energy from an electrical energy source. An electrical insulation layer surrounds the elongate member along the device proximal region. An electrode tip is coupled to the distal end of the elongate member for delivering the energy, the electrode tip being configured and sized for delivering the energy in a manner such that electrical arcing is generated in the region of tissue in order to create a channel through at least a portion of the region of tissue. An electrically insulative thermal shield is disposed between the electrode tip and the device proximal region for preventing arcing therebetween during the delivery of the energy and for thermally protecting the device proximal region from heat produced by the delivery of the energy through the electrode tip.

12 Claims, 10 Drawing Sheets

Related U.S. Application Data

7,947,040, which is a continuation-in-part of application No. 10/666,301, filed on Sep. 19, 2003, now Pat. No. 7,048,733, and a continuation-in-part of application No. 10/760,479, filed on Jan. 21, 2004, now Pat. No. 7,270,662, and a continuation-in-part of application No. 10/666,288, filed on Sep. 19, 2003, now abandoned, which is a continuation-in-part of application No. 10/347,366, filed on Jan. 21, 2003, now Pat. No. 7,112,197, application No. 12/926,292, which is a continuation-in-part of application No. 11/627,406, filed on Jan. 26, 2007.

(60) Provisional application No. 60/596,297, filed on Sep. 14, 2005, provisional application No. 60/743,181, filed on Jan. 27, 2006, provisional application No. 60/827,458, filed on Sep. 29, 2006.

(51) Int. Cl.
*A61B 17/00* (2006.01)
*A61B 18/12* (2006.01)

(52) U.S. Cl.
CPC ............... *A61B 2018/00136* (2013.01); *A61B 2018/1213* (2013.01); *C08L 2201/12* (2013.01)

(56) References Cited

U.S. PATENT DOCUMENTS 4,896,671 A * 1/1990 Cunningham et al. ....... 600/374
5,230,349 A * 7/1993 Langberg ...................... 607/122
5,300,068 A * 4/1994 Rosar et al. .................... 606/34
5,318,525 A * 6/1994 West et al. ................. 604/95.04
5,327,905 A * 7/1994 Avitall .......................... 600/585
5,555,618 A * 9/1996 Winkler .......................... 29/825
5,810,764 A * 9/1998 Eggers et al. .................. 604/23
5,836,875 A * 11/1998 Webster, Jr. .................. 600/374
5,957,842 A * 9/1999 Littmann et al. ............. 600/381
5,967,976 A * 10/1999 Larsen ................. A61B 5/0422 600/374
6,017,340 A * 1/2000 Cassidy et al. ................. 606/47
6,030,380 A * 2/2000 Auth et al. ...................... 606/41
6,217,575 B1 * 4/2001 DeVore et al. ................. 606/41
6,267,758 B1 * 7/2001 Daw et al. ...................... 606/42
6,419,674 B1 * 7/2002 Bowser .................. A61N 1/057 606/45
6,475,214 B1 * 11/2002 Moaddeb ........................ 606/41
2002/0035361 A1 * 3/2002 Houser et al. .................. 606/15
2002/0087153 A1 * 7/2002 Roschak et al. ................ 606/27
2002/0198521 A1 * 12/2002 Maguire ......................... 606/41
2003/0040742 A1 * 2/2003 Underwood et al. ........... 606/32
2004/0024396 A1 * 2/2004 Eggers ............................ 606/39
2004/0143256 A1 * 7/2004 Bednarek ........................ 606/41
2004/0181213 A1 * 9/2004 Gondo ............................ 606/33
2004/0230188 A1 * 11/2004 Cioanta et al. ................. 606/34
2005/0203507 A1 * 9/2005 Truckai et al. ................. 606/51
2006/0142756 A1 * 6/2006 Davies et al. .................. 606/45
2007/0123964 A1 * 5/2007 Davies .................. A61B 5/062 607/116
2007/0270791 A1 * 11/2007 Wang et al. .................... 606/41
2008/0275439 A1 * 11/2008 Francischelli et al. ......... 606/34
2009/0138009 A1 * 5/2009 Viswanathan ..... A61B 18/1492 606/41

OTHER PUBLICATIONS

J. E Della, "Notice of Allowance in the case of U.S. Appl. No. 11/520,754", Jul. 2, 2010.
R. D Gibson, "Non-final rejection in the case of U.S. Appl. No. 11/265,304", Jun. 26, 2009.
R. D Gibson, "Non-final rejection in the case of U.S. Appl. No. 11/265,304", Feb. 5, 2010.
R. D Gibson, "Non-final rejection in the case of U.S. Appl. No. 11/265,304", Jul. 22, 2010.
R. D Gibson, "Notice of allowance in the case of U.S. Appl. No. 11/265,304", Jan. 14, 2011.
M. F Peffley, "Final rejection in the case of U.S. Appl. No. 10/666,301", Sep. 16, 2005.
M. F Peffley, "Notice of Allowance in the case of U.S. Appl. No. 10/666,301", Dec. 23, 2005.
P. J Vrettakos, "Non-final rejection in the case of U.S. Appl. No. 10/760,479",Feb. 14, 2006.
P. J Vrettakos, "Final rejection in the case of U.S. Appl. No. 10/760,479", Oct. 5, 2006.
P. J Vrettakos, "Notice of allowance in the case of U.S. Appl. No. 10/760,479", May 2, 2007.
P. J Vrettakos, "Notice of allowance in the case of U.S. Appl. No. 10/760,479", Jul. 19, 2007.
P. J Vrettakos, "Non-final rejection in the case of U.S. Appl. No. 10/666,288", Nov. 2, 2005.
P. J Vrettakos, "Final rejection in the case of U.S. Appl. No. 10/666,288", Jun. 27, 2006.
P. J Vrettakos, "Non-final rejection in the case of U.S. Appl. No. 10/666,288", Sep. 13, 2006.
P. J Vrettakos, "Final rejection in the case of U.S. Appl. No. 10/666,288", May 21, 2007.
P. J Vrettakos, "Notice of abandonment in the case of U.S. Appl. No. 10/666,288", Dec. 10, 2007.
M. P Straightiff, "Non-final rejection in the case of U.S. Appl. No. 10/347,366", Oct. 4, 2004.
M. P Straightiff, "Final rejection in the case of U.S. Appl. No. 10/347,366", Mar. 21, 2005.
M. P Straightiff, "Non-final rejection in the case of U.S. Appl. No. 10/347,366", Sep. 26, 2005.
M. P Straightiff, "Notice of Allowance U.S. Appl. No. 10/347,366", Feb. 27, 2006.
A. L Scott, "Non-final rejection in the case of U.S. Appl. No. 10/627,406", Oct. 5, 2010.
A. L Scott, "Final rejection in the case of U.S. Appl. No. 10/627,406", Apr. 25, 2011.
A. L Scott, "Notice of Allowance in the case of U.S. Appl. No. 10/627,406", Aug. 17, 2011.

* cited by examiner

ELECTROSURGICAL DEVICE FOR CREATING A CHANNEL THROUGH A REGION OF TISSUE AND METHODS OF USE THEREOF

REFERENCES TO PARENT AND CO-PENDING APPLICATIONS

This application is a Continuation-in-part of U.S. patent application Ser. No. 11/520,754, filed on Sep. 14, 2006, now U.S. Pat. No. 7,828,796, which is a continuation-in-part of U.S. patent application Ser. No. 11/265,304, filed Nov. 3, 2005, now U.S. Pat. No. 7,947,040, which is a continuation-in-part of U.S. application Ser. No. 10/666,301, filed Sep. 19, 2003, now U.S. Pat. No. 7,048,733, and which is a continuation-in-part of U.S. application Ser. No. 10/760,479, filed Jan. 21, 2004, and which is a continuation-in-part of U.S. application Ser. No. 10/666,288, filed Sep. 19, 2003, which is a continuation-in-part of U.S. application Ser. No. 10/347,366, filed Jan. 21, 2003, now U.S. Pat. No. 7,112,197. Ser. No. 11/520,754 also claims the benefit of U.S. provisional patent application Ser. No. 60/596,297, filed Sep. 14, 2005. All of these US patent applications and provisional patent application are hereby incorporated by reference in their entirety.

This application is also a Continuation-in-part of U.S. patent application Ser. No. 11/627,406, now U.S. Pat. No. 8,092,450, which claims the benefit of U.S. Provisional Patent Application Ser. No. 60/743,181, filed on Jan. 27, 2006 and U.S. Provisional Patent Application Ser. No. 60/827,458, filed on Sep. 29, 2006. The patent application and provisional patent applications are all hereby incorporated by reference in their entirety.

TECHNICAL FIELD

The disclosure relates to an electrosurgical device. More specifically, it relates to an electrosurgical device for applying electrical energy to cut through tissue in a region of a patient's body.

BACKGROUND OF THE ART

U.S. Pat. No. 5,300,068 granted to Rosar et al. discloses an electrosurgical apparatus for cutting tissues and for ablating vascular occlusions. Rosar discloses a guide wire that includes a flexible wire with an electrically insulating coating over sections of the wire. The end portion of the wire is received in a bore of an electrically and thermally insulating tip. The distal end of the wire is substantially flush with the distal end of the tip. The distal end of the wire exposed at the distal end of the tip forms an electrode. However, Rosar et al. do not disclose an electrode that is formed/positioned distal to the electrically and thermally insulating tip. The electrode of Rosar is surrounded by the electrically and thermally insulating tip. Furthermore, the electrode of Rosar has a diameter that is less than the outer diameter of the tip. Rosar et al. do not teach an electrode having a diameter that is at least equal to that of the device distal end. Thus, the apparatus of Rosar et al. does not provide an electrode for creating a channel in tissue that can allow the device distal end to be advanced without hindrance through the tissue. Additionally Rosar et al. do not disclose an electrode distal to the insulating tip that secures the tip and allows the tip to be held in place.

U.S. Pat. No. 5,230,349 granted to Langberg discloses an electrical heating catheter having an active electrode that is partially covered by a heat conducting and electrically insulating heat-sink layer for localizing and controlling an electrical heating of tissue and cooling of the active electrode by convective blood flow. The cooling provided by the heat-sink layer increases the depth and volume of an ablation region. Langberg discloses an active electrode designed for electrical heating of tissue for ablation. However, Langberg does not teach an electrode tip operable to create a channel through tissue. Additionally, Langberg discloses a heat-sink layer that functions to increase the depth and volume of ablation. However, Langberg does not teach a thermal shield for protecting the insulated portion of the catheter.

BRIEF DESCRIPTION OF THE DRAWINGS

In order that the invention may be readily understood, embodiments of the invention are illustrated by way of examples in the accompanying drawings, in which.

SUMMARY OF THE INVENTION

Figure 1A:
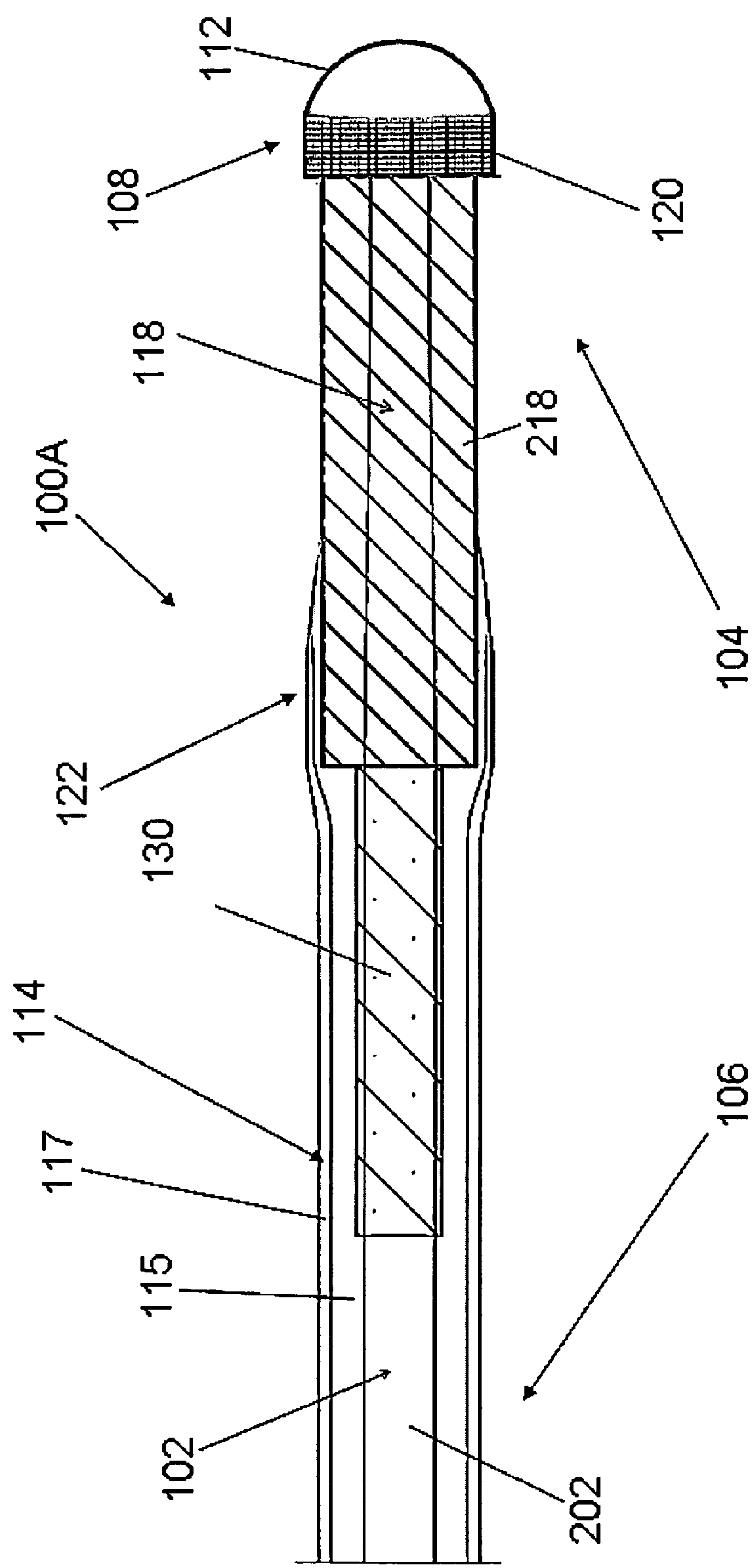
FIG. 1A-1B are an illustration of an electrosurgical device in accordance with an embodiment of the present invention.

In one broad aspect, embodiments of the present invention comprise an electrosurgical device for creating a channel through a region of tissue using energy provided by an electrical energy source, the device defining a device proximal region and a device distal region. An electrically conductive elongate member is provided for receiving the energy from the electrical energy source, the elongate member defining a distal end provided in the device distal region. In addition, an electrical insulation layer surrounds the elongate member along the device proximal region. Furthermore, an electrode tip is electrically coupled to the distal end for delivering the energy, the electrode tip being configured and sized for delivering the energy in a manner such that electrical arcing is generated in the region of tissue in order to create a channel through at least a portion of the region of tissue when the electrode tip is positioned proximate the region of tissue. In this context, "proximate" should be understood to mean that the electrode tip is positioned either substantially adjacent to the tissue or slightly spaced apart from the tissue such that a gap exists between the tissue and the electrode tip. The device is further provided with an electrically insulative thermal shield disposed between the electrode tip and the device proximal region for preventing arcing therebetween during the delivery of the energy and for thermally protecting the device proximal region from heat produced by the delivery of the energy through the electrode tip.

As a feature of this broad aspect, in some embodiments, the thermal shield has a thermal conductivity of about 1 W/m-K or more.

As another feature of this broad aspect, in some embodiments, the thermal shield has a thermal conductivity of about 2 W/m-K or more. As an example of this feature, the thermal shield comprises single crystal aluminum oxide.

As still another feature of this broad aspect, in some embodiments, the electrode tip is configured and sized for generating a current density sufficient for initiating arcing at the electrode tip during the delivery of the energy, thereby allowing the device to create the channel through the at least a portion of the region of tissue. As an example of this feature, the electrode tip is shaped substantially like a segment of a sphere.

As a feature of this broad aspect, in some embodiments, the elongate member is fabricated from a shape memory alloy. As an example of this feature, the shape memory alloy comprises a nickel-titanium alloy such as the alloy commercially referred to as Nitinol™. As another example of this feature, the elongate member is shape-set to a preset curvature.

As an additional feature of this broad aspect, in some embodiments, the electrosurgical device is provided with a radiopaque band positioned proximally with respect to the thermal shield. As an example of this feature, the radiopaque band is operatively coupled to the elongate member adjacent the thermal shield to support the thermal shield on the elongate member.

As still an additional feature of this broad aspect, in some embodiments, the electrode tip is formed integrally with the elongate member. In some embodiments, the elongate member and electrode tip both comprise a shape memory nickel-titanium alloy such as Nitinol™.

As still an additional feature of this broad aspect, in some embodiments, the electrosurgical device is further provided with a support structure positioned distally with respect to the thermal shield for supporting the electrode tip.

In some embodiments, the support structure is electrically conductive. In one specific example, the support structure comprises tantalum.

In some embodiments, the electrode tip is attached to the support structure. In one specific example, the electrode tip is laser welded to the support structure. As an additional feature of this specific example, the electrode tip is fabricated from a shape memory nickel titanium alloy. As still an additional feature of this specific example, the electrode tip is formed by laser welding the distal end onto the support structure. As still an additional feature of this specific example, the support structure comprises tantalum.

In some embodiments, the support structure is radiopaque.

As still an additional feature of this broad aspect, in some embodiments, the electrode tip and the thermal shield define respectively a tip outer diameter and a shield outer diameter, the tip outer diameter being greater than or equal to the shield outer diameter. In some embodiments, the tip outer diameter is greater than the shield outer diameter.

As still an additional feature of this broad aspect, in some embodiments, the device proximal region defines a proximal region maximal diameter and the electrode tip defines a tip diameter, the proximal region maximal diameter being greater than the tip diameter. Put differently, the maximum diameter of the device proximal region is greater than the tip diameter.

As another feature of this broad aspect, in some embodiments, the electrical insulation layer overlaps a portion of the thermal shield.

As another feature of this broad aspect, in some embodiments, the thermal shield is radiopaque.

As still another feature of this broad aspect, in some embodiments, a portion of the electrosurgical device is coated with a hydrophilic coating.

As still another feature of this broad aspect, in some embodiments, the electrosurgical device has a predefined curvature.

In another broad aspect, a method is described for creating a channel through an occlusion located in a body vessel of a patient, the occlusion including an occlusion harder portion and an occlusion softer portion. The method uses a channel creating apparatus defining an apparatus distal end portion insertable into the body vessel and the channel creating apparatus includes an energy delivery component operatively coupled to the apparatus distal end portion for delivering energy proximate the apparatus distal end portion. The method is accomplished by positioning the apparatus distal end portion proximate the occlusion, creating a harder portion channel through the occlusion harder portion by delivering energy into the occlusion harder portion using the energy delivery component, and creating a softer portion channel through the occlusion softer portion by advancing the apparatus distal end portion through at least a portion of the occlusion softer portion substantially without using the energy delivery component to deliver energy into the occlusion softer portion.

As a feature of this broad aspect, in some embodiments, arcing is initiated at the energy delivery component during the step of delivering energy into the occlusion harder portion to create the harder portion channel.

As another feature of this broad aspect, in some embodiments, the step of creating the softer portion channel is performed before the step of creating the harder portion channel.

In another broad aspect, embodiments of the present invention comprise a method for creating a channel through an occlusion located in a body vessel of a patient. The method uses a channel creating apparatus defining an apparatus distal end portion insertable into the body vessel, the channel creating apparatus including an energy delivery component operatively coupled to the apparatus distal end portion for delivering energy proximate the apparatus distal end portion. The method is accomplished by: (i) positioning the apparatus distal end portion proximate the occlusion; (ii) testing the occlusion to determine whether the apparatus distal end portion can be advanced through the occlusion (A) by the application of mechanical force or (B) by delivering energy into the occlusion using the energy delivery component; (iii) creating a channel portion through at least a portion of the occlusion by (A) or (B) as determined in step (ii).

In another broad aspect, embodiments of the present invention describe an energy delivery device for creating a channel through a region of tissue using energy provided by an electrical energy source. The device defines a device proximal region and a substantially opposed device distal region, the device proximal region including an electrical insulator at a radial periphery thereof. In other words, the term "device proximal region" as used herein includes the electrical insulator or insulation layer located in that region. Furthermore, the device distal region defines a distal end and the device further includes an energy delivery means for coupling to the energy source, the energy delivery means being positioned at the distal end for delivering energy to the region of tissue. In such an embodiment (i.e. where the electrode tip is at the distal end of the device), the energy delivery means, once positioned, can be understood to itself form the distal end of the complete device. The energy delivery means is shaped to provide a current density sufficient to initiate arcing at the energy delivery means during the delivery of energy allowing the device to create a channel through at least a portion of the region of tissue. The device further includes an electrical and thermal protection means positioned between the device proximal region and the energy delivery means for electrically and thermally protecting the device proximal region from the arcing initiated at the energy delivery means during the delivery of energy.

In another broad aspect, embodiments of the present invention comprise an electrosurgical device for creating a channel through a region of tissue, the device comprising: an elongate member comprising a nickel-titanium alloy operable to be coupled to an energy source and having a distal end; an electrical insulation layer disposed onto the elongate member along a substantial portion thereof including along a device proximal region; an electrode tip coupled to the elongate member distal end for delivering energy to the region of tissue to create a channel through at least a portion of the tissue; an electrically insulative thermal shield disposed between the electrode tip and the device proximal region for preventing arcing therebetween during the delivery of energy and for thermally protecting the device proximal region from heat produced by the delivery of energy through the electrode tip, the thermal shield having a thermal conductivity of greater than about 2 W/m-K; and a tantalum support structure positioned distal to the thermal shield for supporting the electrode tip; wherein the electrode tip is formed by laser welding the elongate member distal end onto the support structure allowing the electrode tip to be laser welded to the support structure and whereby the electrode tip is shaped substantially like a segment of a sphere.

In a yet further aspect, embodiments of a method of creating a channel through an occlusion located in a body vessel of a patient are described. In such embodiments, the method uses an electrosurgical device wherein the electrode tip and the thermal shield define respectively a tip outer diameter and a shield outer diameter, the tip outer diameter being greater than or equal to the shield outer diameter. In addition, the electrosurgical device is insertable into the body vessel and operable to deliver energy through the electrode tip and the electrosurgical device defines a device distal region comprising the electrode tip and the thermal shield. The method is performed by: creating a channel portion through the occlusion by delivering energy through the electrode tip, the channel portion being at least as wide as the tip outer diameter to allow at least the electrosurgical device distal region to be advanced through the occlusion.

DETAILED DESCRIPTION

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The description provided herein below for device 100 should be understood by a person skilled in the art to apply to any one of the devices 100A-100E illustrated in the accompanying figures, unless otherwise indicated.

In accordance with an embodiment of the present invention, as shown in FIG. 1A, an electrosurgical device 100A is provided. The electrosurgical device comprises an inner elongate member 102 (also referred to generally as an "elongate member") which is an electrical conductor. A thermal shield 118 is positioned at the distal end of the elongate member. An electrode tip 112 is coupled to the distal end of the elongate member 102 distal to the thermal shield 118. In some embodiments, a support structure 120 is positioned distal to the thermal shield 118 for supporting the electrode tip 112. The elongate member has an insulation layer 114 disposed along a portion thereof including along a proximal region 106 of the device. The device proximal region is the portion of the device 100 that is proximal to the heat shield 118.

Figure 7A:
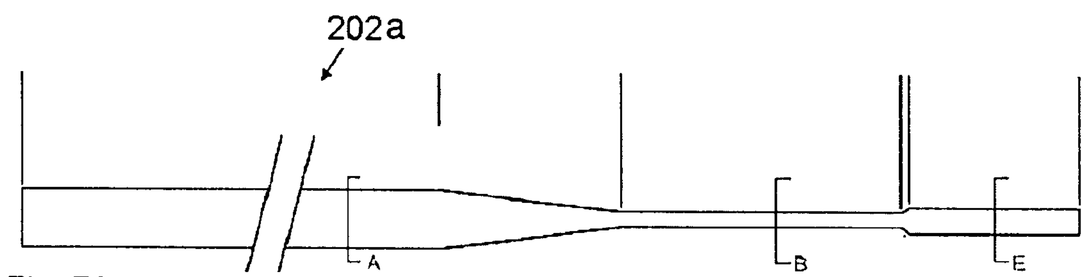
FIGS. 7A-7C show an elongate member of an electrosurgical device in accordance with various embodiments of the present invention.

The inner elongate member 102 extends longitudinally and has a proximal end operable to be coupled to an energy source (not shown in the drawings) and a distal end coupled to an energy delivery component, such as an electrode having an electrode tip 112. In one embodiment, the inner elongate member 102 may comprise a core wire 202. In one example, the core wire 202 may comprise a shape memory alloy, such as a nickel-titanium alloy. One example of a nickel-titanium alloy is Nitinol™. In another example, the core wire 202 may comprise stainless steel. Alternatively, any other suitable material may be used for core wire 202. In some embodiments the elongate member 102 may have an outer profile defined by a uniform or constant outer diameter along its length. In other embodiments, the elongate member 102 may have a variable outer diameter along its length. In some examples, the core wire has varying outer diameters along its length as shown by core wires 202*a*-202*c* in FIGS. 7A-7C. This may provide varying degrees of stiffness and flexibility along different sections of the core wire 202. The varying diameters of the core wire 202 and the thickness of the insulation layer 114 along the distal region of the device can help control/modify the stiffness of the device distal region. A smaller outer diameter in a section of the core wire 202 may provide increased flexibility of the wire in that region and may allow the wire to be floppier in that region. In one example, the core wire 202 has sufficient flexibility to allow the device 100 to conform to the vasculature of a patient and has sufficient rigidity to allow pushability of the device 100 through tissue. Alternatively, the elongate member 102 may have any other suitable profile. In one example, the elongate member 102 comprises a solid electrical conductor, to allow for increased rigidity. In another example, the elongate member 102 may be substantially hollow.

In some embodiments of the present invention the electrosurgical device 100 may have a predefined curvature. A portion of the electrosurgical device such as distal region 104 can be provided with varying degrees of curvature which may help in navigation of the device 100 through vasculature. In one example, the curvature of the electrosurgical device 100 may facilitate the device 100 engaging with an occlusion located in peripheral vasculature. In one specific example, the curvature of the electrosurgical device 100 may allow the device 100 to engage an occlusion located at or near a bifurcation in a body vessel. In some embodiments, the curvature of device 100 may be provided by fabricating the elongate member 102 from a shape memory alloy that has been shape-set to a preset curvature. In one example, the elongate member 102 may comprise a Nitinol wire which may be shape set with the specific angle of curvature or shape that is needed. In embodiments where a shape memory alloy such as Nitinol wire is used, the shape memory alloy can be treated to have super-elastic properties so that it will not deform permanently when it is pushed against an occlusion. The wire will this revert to its original shape when it is retracted minimizing the risk of the wire distal end being bent out of shape. In other embodiments, the elongate member 102 may have a bend or angle at a location along its length. In still other embodiments, the elongate member 102 may comprise a hollow hypotube such as a metal hypotube that may be laser cut to provide flexibility at the distal tip. In still other embodiments the core wire 202 may comprise a coil disposed onto a distal portion of the core wire 202 in order to increase flexibility in the distal portion. Furthermore, the device 100 may be a steerable device.

In some embodiments, the electrosurgical device 100 may have an insulation layer 114 disposed along a portion of the device 100, such that the insulation layer 114 substantially surrounds the elongate member 102 to minimize leakage of energy along elongate member 102. It should be understood that the term 'surrounds' as used herein can indicate, for example, that the insulation is applied directly to the elongate member or, as another example, that the insulation is applied to some intermediate layer located on the elongate member. In some embodiments the insulation layer 114 is disposed along a majority of the length of the device including along a proximal region 106 of the device. In other embodiments, the insulation layer 114 may be disposed substantially only along the proximal region 106 of the device. The insulation layer 114 helps to electrically insulate a portion of the electrosurgical device 100. This may help protect the patient and the user, for example the physician, from exposure to electrical current during use of device 100. In one example, the insulation layer 114 is disposed onto a core wire 202 of device 100, substantially along a proximal region of device 100. In one embodiment, the insulation layer is disposed onto the elongate member 102 after the distal components, comprising the thermal shield 118, the electrode tip 112 and/or support structure 120, have been coupled to or formed onto the elongate member 102 distal end. In other embodiments, the elongate member 102 may be coated with an insulation layer 114 prior to the distal components being coupled to the elongate member distal end. In other words, the elongate member 102 may be provided as an insulated elongate member 102 having an insulation layer 114. In one such example, the thermal shield 118 may be loaded onto a distal end of an insulated core wire 202 that is at least partially insulated. A support structure 120 may be loaded onto the core wire 202 and may be electrically in contact therewith, the support structure 120 being positioned distal to the thermal shield 118. Additionally, an electrode tip 112 may be formed integrally with the core wire 202 onto the support structure 120 as described further hereinbelow. In still other embodiments, the elongate member 102 may be provided as an insulated core wire 202 which can be coated with an additional insulation layer 114 after distal components have been coupled to the core wire 202 distal end.

A variety of materials may be used for the insulation layer 114, including but not limited to polymer or ceramic. A polymer insulation layer 114 may be provided using a heat shrink process or a melt processing method. Alternatively any other suitable method may be used. In some embodiments, the insulation layer 114 may be provided through a dip coating process. A portion of the electrosurgical device 100 or the elongate member 102 may be dipped in a liquid for e.g. a liquid polymer such as liquid PTFE or a ceramic. In other embodiments, a portion of the device 100 or the elongate member 102 may be spray coated with an insulative material for e.g. a polymer or a ceramic. In still other embodiments, a vapor deposition technique may be used to form the insulation layer 114. In some embodiments, where an insulated elongate member 102 is provided, the elongate member 102 may be dip coated with a polymer or insulated with a thin PTFE layer to form the insulated elongate member 102.

Figure 1B:
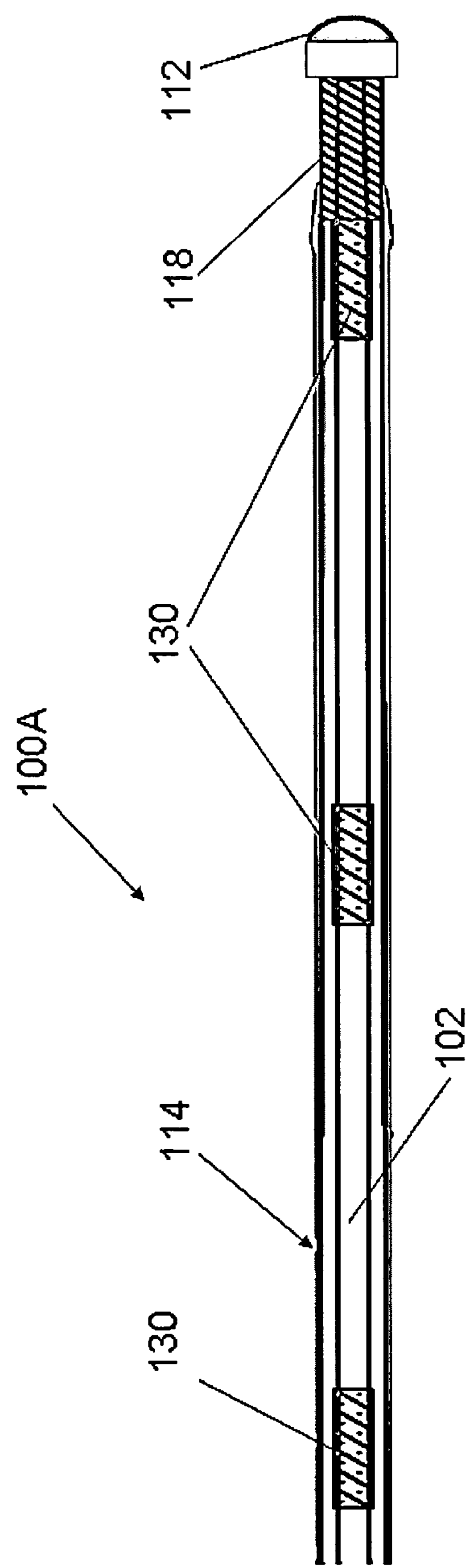

In one embodiment, a polymer combination may be used for the insulation layer 114. As an example, a two layer heat shrink layer may be used comprising an inner polymer layer 115 and an outer polymer layer 117. In another example, the inner polymer layer 115 may comprise a melt-processable polymer that can flow around and into any irregularities on the surface of core wire 202 and the outer polymer layer 117 may comprise a heat recoverable polymer. In a specific instance of this example, the insulation layer 114 comprises a combination of FEP and PTFE polymers, where the inner polymer layer 115 comprises FEP and the outer polymer layer 117 comprise PTFE as shown in FIG. 1A. A process combining re-flow and heat-shrink is used and the dual polymer layer is heated to a temperature of about 660° F., allowing the inner FEP layer to flow around and encapsulate the one or more radiopaque bands 130 disposed on core wire 202. Whereas, the outer PTFE layer recovers to a pre-specified diameter around the FEP and provides a smooth outer finish. In another instance of this example, PEBAX may be used as a melt-processable inner polymer layer. In one embodiment, one or more radiopaque bands 130 may be disposed along the core wire 202. The radiopaque bands 130 may comprise, for example, radiopaque material such as gold, iridium or platinum. In one example, a plurality of platinum radiopaque bands 130, are disposed along the core wire 202, as shown in FIG. 1B. In one embodiment, the insulation layer 114 may be disposed over the radiopaque bands 130. The insulation layer 114 may provide a smooth outer profile for the electrosurgical device 100.

In one embodiment of the present invention, a portion of the electrosurgical device 100 may have a hydrophilic coating disposed thereon. This may help make the device lubricious and may help the device 100 to traverse through vasculature or through tissue, for e.g. an occlusion. The insulation layer 114 may comprise a material that allows a hydrophilic coating to be disposed thereon. In some embodiments the insulation layer 114 may comprise a polymer such as PEBAX, FEP or other non-fluoro polymers onto which a hydrophilic coating can be applied. In some embodiments, as mentioned previously, a combination of polymer layers may be used to form the insulation layer 114, for e.g. an inner polymer layer 115 and an outer polymer layer 117. In other examples, any number or combination of polymer layers may be possible. In such embodiments, the outer polymer layer may comprise a material that can be coated with a hydrophilic coating. Some non-limiting examples include an inner polymer layer 115 of PTFE and an outer polymer layer 117 of either FEP or Pebax, or an inner polymer layer 115 of FEP and an outer layer of Pebax. In some embodiments, the inner polymer layer 115 may provide electrical insulation and the outer polymer layer 117 may allow the device 100 to be coated with a hydrophilic coating. In some embodiments, entire device 100 may be coated with a hydrophilic coating. In other embodiments, the distal region 104 of the device 100 may have the hydrophilic coating which may include the thermal shield 118. In other words, the distal region 104 may be made lubricious. In a non-limiting example, the hydrophilic coating may comprise Hyaluronic Acid (HA).

In one embodiment, as shown in FIG. 1A, the electrosurgical device 100 defines a distal region 104 having a heat shield or heat sink 118 disposed at or near the distal end of the core wire 202 substantially distal to the insulation layer 114. In this embodiment, the heat shield or heat sink 118 is positioned between the insulation layer 114 and the energy delivery component, such as electrode tip 112 positioned at the distal end of core wire 202. The heat shield 118 can also be referred to as an electrically insulative thermal shield.

The heat shield 118 is an electrical and thermal insulator that functions to insulate and thus protect the device proximal region 106, for example the insulation layer 114 located in proximal region 106, from the heat generated at the electrode tip 112 and functions to prevent arcing between the electrode tip and the device proximal region 106. The device proximal region is the portion of the device that is proximal to the heat shield 118. In some embodiments, the heat shield 118 has a thermal conductivity that allows the heat shield 118 to dissipate heat by effectively conducting heat away from the electrode tip 112. This may prevent the heat shield 118 from being damaged due to excessive heat generated at the electrode tip 112.

In one embodiment, the heat shield has a thermal conductivity k, that is greater than about 1 Watt/mK. In other embodiments, the heat shield has a thermal conductivity k that is greater than about 2 Watts/mK. In some embodiments the heat shield 118 may comprise glass or a ceramic such as alumina, aluminum oxide, zirconia toughened alumina (ZTA) or zirconium oxide. In one example, the heat shield 118 comprises a ceramic 218 that is made of pure alumina or sapphire crystal comprising a single/mono crystal aluminum oxide. In other embodiments, other ceramics such as Silicon Nitride or Silicon Carbide may be used. In still other embodiments, any other suitable ceramic may be used as heat shield 218. In still other embodiments, the heat shield 118 may comprise any other suitable insulative material that is not damaged by the temperatures generated at electrode tip 112. Additionally, in some embodiments, the heat shield 118 has sufficient mechanical strength which may allow it to be machined into the desired shape such as a tubular cylindrical shape.

In one embodiment, the electrode tip 112 is a mono-polar active electrode. When arcing is initiated at the mono-polar active electrode, high temperatures are created at the electrode tip 112 and within the region of tissue surrounding the electrode tip 112. The ceramic heat shield 218 is thermally insulative and withstands the high temperatures generated while maintaining good dielectric properties. In other words, ceramic heat shield 218 additionally functions as an electrical insulator. In some embodiments, the thermal conductivity of ceramic heat shield 218 is sufficient to allow heat to be dissipated away from the active electrode tip 112 while minimizing transmission of heat to the device proximal region 106 having the insulation layer 114. Thus, a proximal segment of the electrosurgical device 100 is effectively shielded from arcing at the electrode tip 112 as well as from the heat generated at the electrode tip 112. In other words, the ceramic heat shield 218 prevents degradation of the insulation layer 114 as may occur due to its proximity to arcing. Thus, the heat shield 118 acts as a protective barrier between active electrode tip 112 and the insulation layer 114 by electrically insulating the electrode tip 112 from arcing at the electrode tip 112 and by providing thermal protection for the insulation layer 114 by substantially thermally insulating the device proximal region 106 from the electrode tip 112. In other words, in some embodiments, a single thermal shield 118 functions as a barrier between the device proximal region 106 and the electrode tip 112 and provides provide both the benefit of preventing arcing between the device proximal region 106 and the electrode tip 112 as well as protecting the device proximal region from the heat produced by the delivery of energy through the electrode tip 112. In one embodiment, the heat shield 118 functions to electrically and thermally isolate the device proximal region 106 including the insulation layer 114 from the device distal tip 108 including the electrode tip 112.

In one example, the heat shield 118 is a ceramic comprising a tubular single crystal aluminum oxide (sapphire) cylinder 218 that is a thermal insulator having suitable thermal conductivity and mechanical strength. The sapphire ceramic heat shield 218 can support voltages used to initiate arcing and can withstand higher temperatures resulting from arcing at the distal tip 108. Furthermore, the single crystal Aluminum Oxide ceramic (sapphire) heat shield 218 also provides mechanical strength and helps impart rigidity to the distal region 104 of the electrosurgical device. This may help reduce the risk of the heat shield 218 from cracking when the device 100 is pushed or manipulated during the manufacturing process. Thus ceramic heat shield 218 may both provide thermal insulation as well as mechanical strength and/or rigidity. In one specific example, the ceramic heat shield 218 is a single crystal Aluminum oxide heat shield 218 that is a tubular cylinder having a longitudinal length of about 2-3 mm, for example about 2.54 mm. In some such embodiments, the tubular cylindrical ceramic has an inner diameter of about 0.2 to about 0.4 mm, for example about 0.292 mm and an outer diameter of about 0.5 to about 0.8 mm, for example about 0.660 mm. In one embodiment, the heat shield 118 comprises material that can be viewed using an imaging modality. In one such example, the heat shield 118 is radiopaque.

Figure 7B:
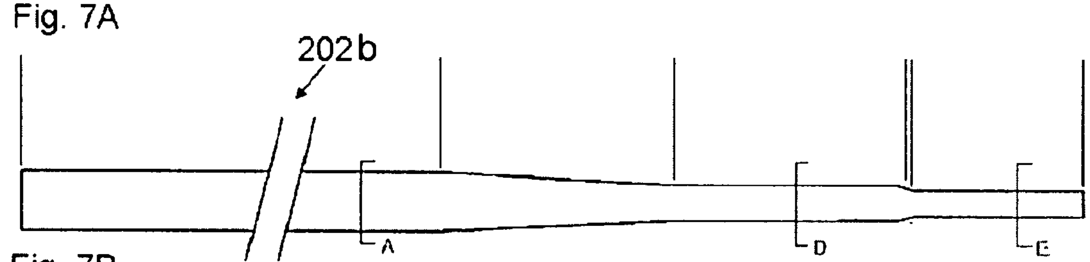
Figure 7C:
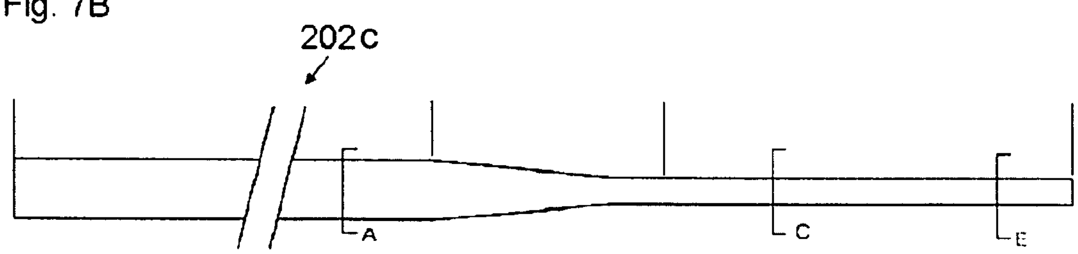

As described above, device 100 may include one or more radiopaque bands 130. The placement of the radiopaque bands 130 onto to the inner core 202 may also help increase rigidity of the device 100. In one embodiment, the combination of the radiopaque bands 130, the core wire 202 and the heat shield 218, provides sufficient rigidity to enhance pushability of device 100 through tissue, for e.g. an occlusion. In one embodiment, a radiopaque band 130 is positioned proximal to the heat shield 118. In one example, the radiopaque band 130 is secured to the core wire 202 to retain/support the heat shield 118 in position. In another example, the heat shield 118 is retained or supported in place by the core wire 202. In such an embodiment, the core wire 202 has a wider section adjacent and proximal to the distal section as shown in FIG. 7B. The heat shield 118 is loaded onto the distal section and retained by this wider section of the core wire 202.

In one embodiment, as shown in FIG. 1B, multiple radiopaque bands 130 are positioned on the core wire 202. These provide reference markings which when viewed under fluoroscopic imaging provide guidance to the physician for positioning the device 100 within a patient's body and/or for advancement of the device 100 during use. The radiopaque bands 130 may comprise materials such as platinum, iridium, gold, silver, tantalum and tungsten or their alloys, or radiopaque polymer compounds. In one specific example, as mentioned above, platinum is used for the radiopaque bands 130.

As illustrated in FIG. 1A, the electrode tip 112 forms the energy delivery component of electrosurgical device 100, via which energy is delivered. As shown, the active electrode tip 112 is positioned distal to the heat sink 118 at the distal tip 108. The distal tip 108 defines the part of the distal region 104 that is distal to the heat sink. A junction 122 is formed forms between the insulation layer 114 and the heat sink 118.

In some embodiments, a seamless transition is provided at the junction 122 between the insulation layer 114 and the ceramic 218. In one embodiment, the insulation layer 114 extends over the heat-shield at the junction 122 as shown in FIG. 1A. Therefore, an overlap of insulation layer 114 forms over the heat-shield 218 forming a sealed junction. In one specific example, the insulation layer overlaps the proximal portion of the heat-shield 218 by about 0.5 mm to about 2 mm, for example about 1 mm. The overlap of the insulation layer 114 at junction 122 with the ceramic heat shield 218 helps to limit the arcing to the electrode tip 112 at the distal tip 108. This may help minimize arcing observed behind the heat shield near the junction 122 and may help minimize degradation of the insulation layer 114 from the heat generated at the electrode tip 112 from the delivery of electrical energy through the electrode tip 112.

Figure 2:
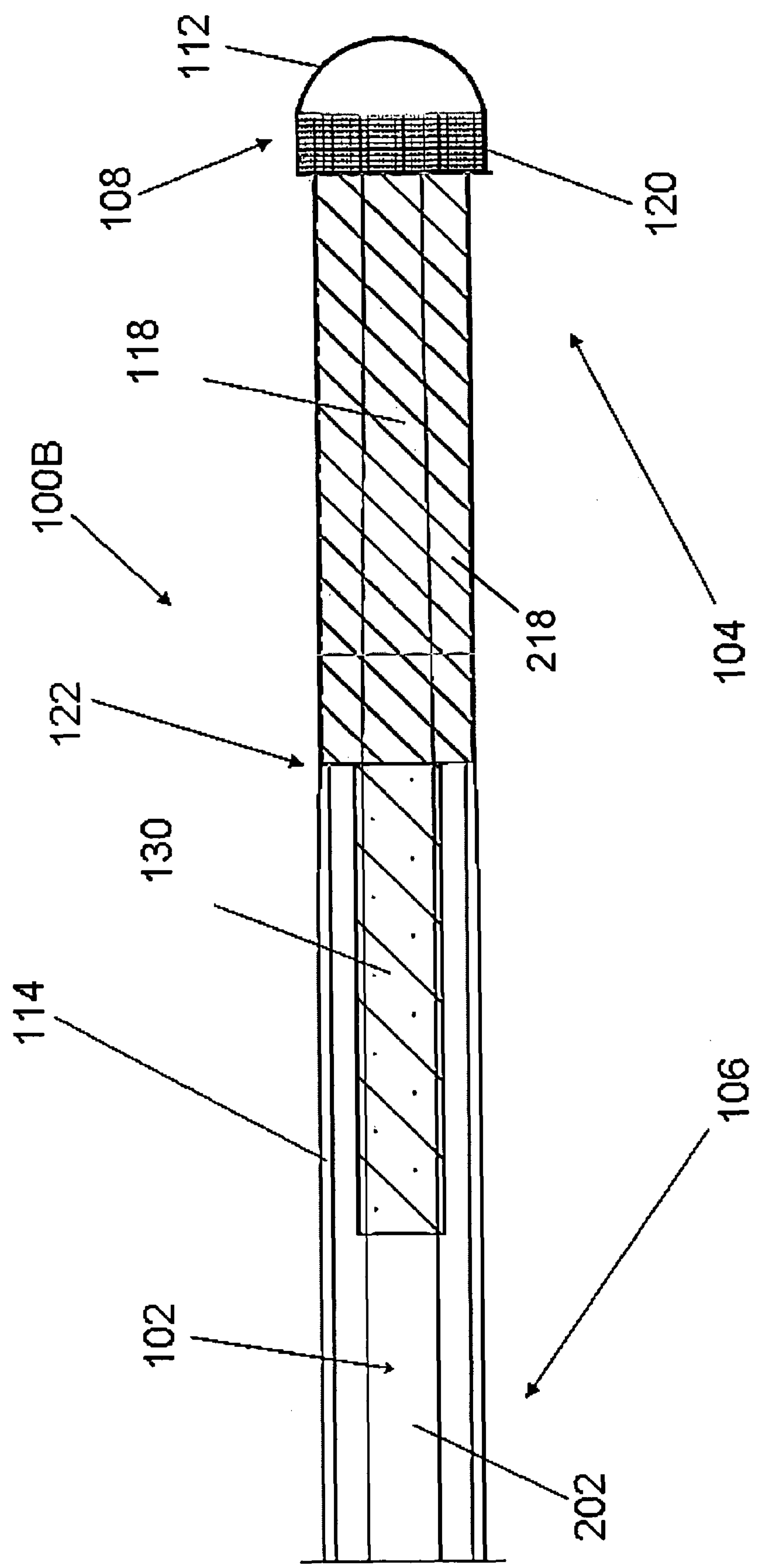
FIG. 2 is an illustration of an electrosurgical device in accordance with an alternate embodiment of the present invention.
Figure 3:
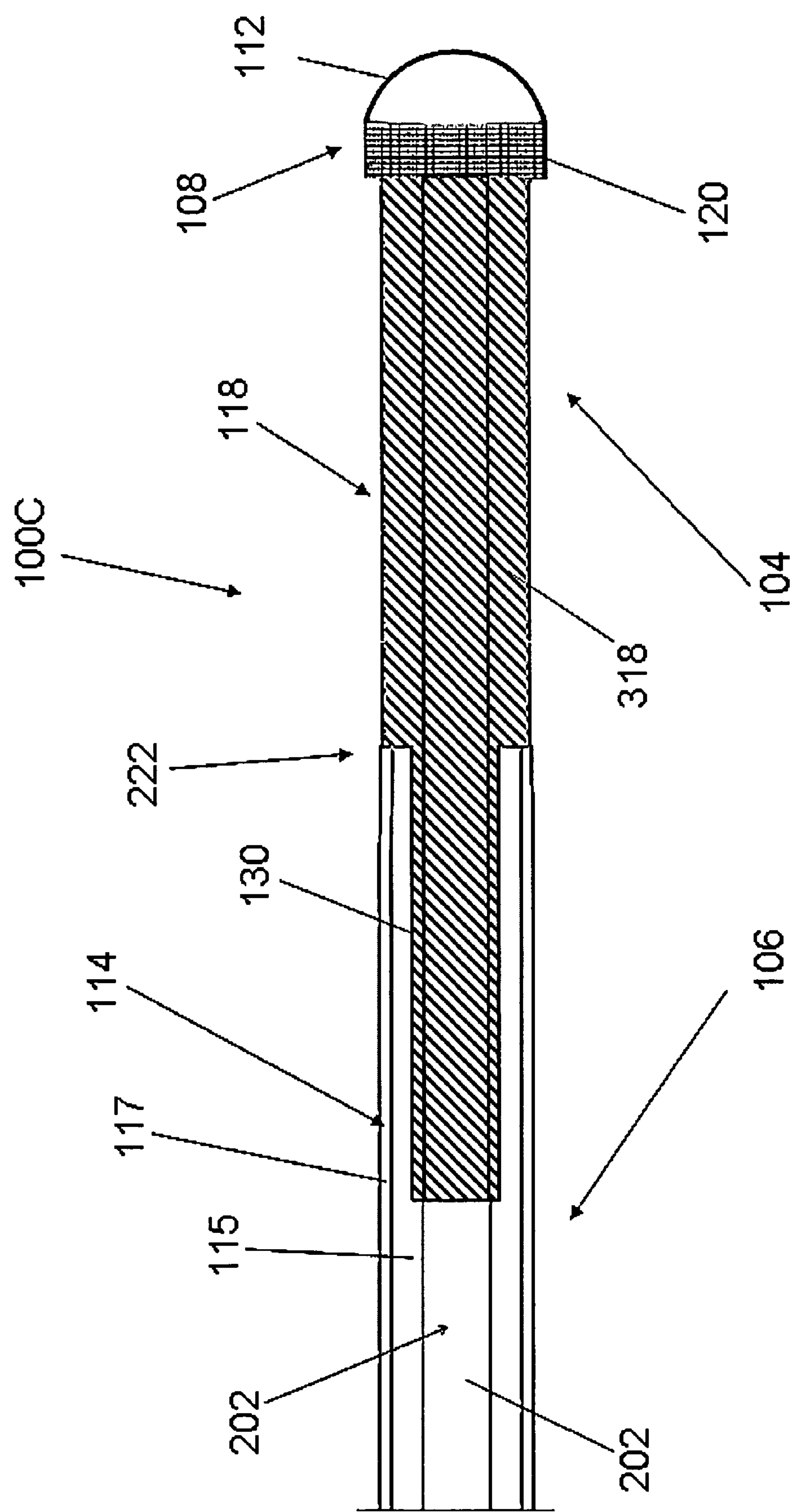
FIG. 3 is an illustration of an electrosurgical device in accordance with an alternate embodiment of the present invention.

In another embodiment, the insulation layer 114 and the heat shield 118 such as ceramic heat shield 218 may be flush against one another (or in other words may abut one another) to form a junction therebetween as shown by device 100B in FIG. 2. In still another embodiment, a step-down heat shield 318 may be used as shown by device 100C in FIG. 3. The heat shield 318 may be a ceramic heat shield having properties similar to those mentioned previously for ceramic heat shield 218 and/or or heat shield 118. In some embodiments, the heat shield 318, for e.g. a tubular ceramic heat shield, is wider at its distal portion than at its proximal portion. This allows the insulation layer 114 to form around the proximal portion of the heat-shield 318. The insulation layer 114 is formed flush against and surrounding the proximal portion of the heat shield 318. This allows for a smooth transition between the heat shield 318 and the insulation layer 114, and may also allow for a secure junction 222 to be formed between the two materials. This helps ensure that the wire 202 is not exposed at the junction 222. This also helps minimize any shoulder effect (also known as 'hot spots') which may otherwise be created between the insulation 114 and the heat shield 318. Thus, the risk of a discontinuity forming due to exposure of wire 202 at the junction 222 is minimized. This allows arcing to be limited the electrode tip 112. Furthermore, the smoother outer profile at the junction 222 may prevent tissue from getting caught and snagging at the junction 222 which may allow device 100 to traverse through the occlusion relatively easily.

In one embodiment of the present invention, energy is supplied from the energy source through the elongate member 102 to the energy delivery component comprising electrode tip 112. The electrode tip 112 is coupled to the elongate member distal end which receives energy from the energy source. The electrode tip 112 is configured and sized such that a sufficiently high current density is provided at the electrode tip 112 to generate arcing in a region of tissue when the electrode tip 112 is positioned proximate the region of tissue. This allows a channel to be created through at least a portion of the region of tissue. In one specific example, the electrode tip 112 has an outer diameter (OD) of between about 0.027" to about 0.032" and a longitudinal length of between about 0.15 mm to about 0.20 mm.

In some embodiments, the electrode tip 112 may be attached to the elongate member distal end. In other embodiments, laser welding is used to form electrode tip 112 at the distal end of the elongate member. In still other embodiments, other methods may be used to provide the electrode tip 112. In some embodiments the electrode tip 112 defines the electrode. In other words, the electrode tip 112 forms the energy delivery component of electrosurgical device 100. In one embodiment, the electrode tip 112 comprises a segment of a sphere, i.e. it is substantially spherical in shape. For example, substantially the entire energy delivery portion comprising the electrode tip 112 (i.e. the entire surface from which energy is delivered) forms a segment of a sphere. For example, the electrode tip 112 is a hemispherical or a rounded electrode tip 112 as shown in FIGS. 1-4, 8 and 9A. The shape and surface area of the electrode tip 112 allow the current density, and thus arcing, to be focused/concentrated at the distal most tip. Put differently, the electrode tip 112 comprises a dome shaped electrode tip 112 which allows for increased current density at the distal most tip, which facilitates the initiation of arcing and thereby allows the electrosurgical device 100 to create a channel through tissue.

Figure 9B:
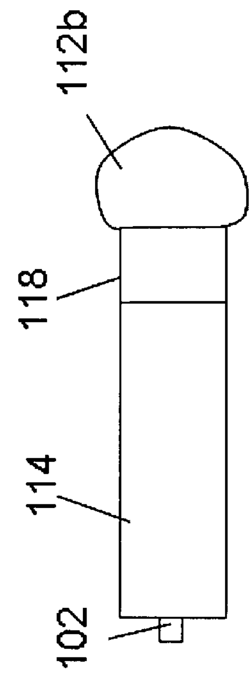
FIGS. 9A-9E show the electrode in accordance with various embodiments of the present invention.

As described above, and as shown in FIG. 9A, the electrode tips 112*a* and 112*a*' are shaped substantially as a segment of a sphere. In an alternate embodiment, the electrode tip 112*b* may comprise a "mushroom shaped" tip as shown in FIG. 9B. Furthermore, in some embodiments, the tip 112 is substantially atraumatic, for e.g. as shown by electrode tips 112*a* and 112*a*'. In another embodiment, the electrode tip 112*c* may comprise a bi-arcuate tip, as shown in FIG. 9C. A laser weld process may be used that allows a cavity or bowl to be formed at the center of the electrode tip 112*c* which may allow electrical energy and thus increased current density to be concentrated within the cavity. Thus arcing may be concentrated at the central region of the electrode tip 112*c*.

In some embodiments, a support structure 120 may be positioned adjacent the elongate member 102 distal end, distal to the heat shield 118 and laser welding may be used to form electrode tip 112*c* onto the support structure. Similarly, in some of the other embodiments shown in FIGS. 9A-9D, the electrode tip 112 may be formed by laser-welding the distal end of the core wire 202 onto a support structure 120 positioned distal to the heat shield 118.

Figure 9D:
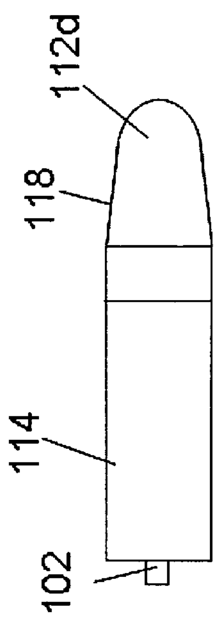
Figure 9E:
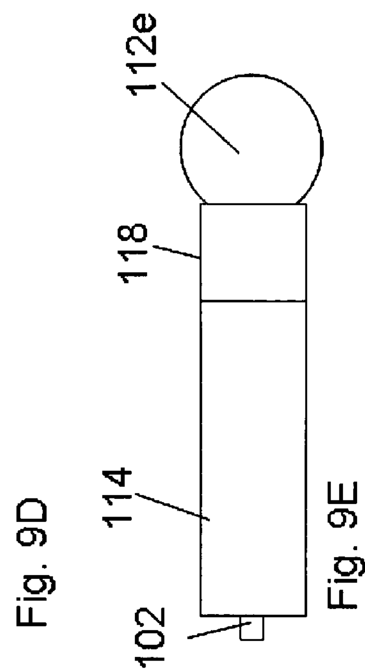
Figure 9A:
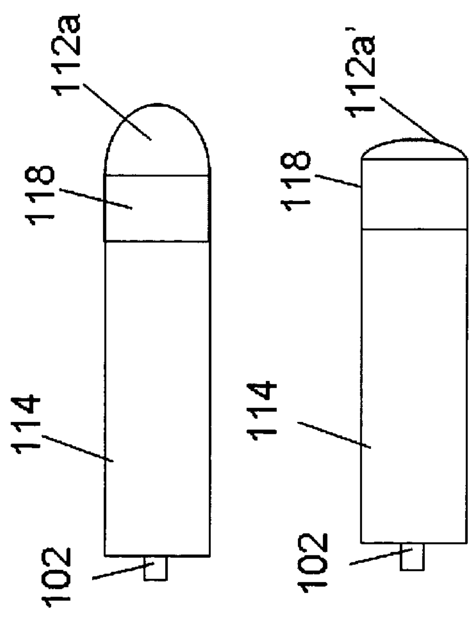
Figure 9C:
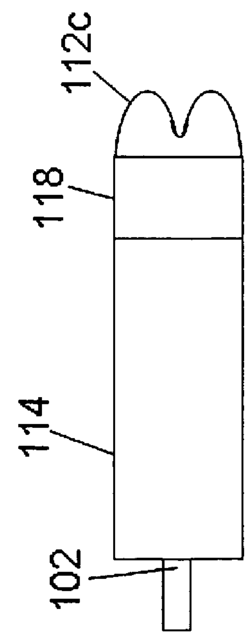

In a further embodiment, the electrode tip 112*d* forms a conical shape and tapers towards its distal end as shown in FIG. 9D. This may allow arcing to be concentrated at the distal most end of the electrode tip 112*d* having a lower surface area and thus a higher current density. In one example, as shown in FIG. 9D, the distal most end of the conical electrode tip 112*d* may be rounded in shape. This may allow the electrode tip 112 to be substantially atraumatic when inserted for example, into the body vasculature. In an alternate embodiment, an electrode tip 112*e* may comprise a ball shaped electrode, as shown in FIG. 9E. In some embodiments, the electrode tip 112 may have a surface geometry that allows sufficient current density to accumulate the electrode tip 112 that is sufficient to generate arcing to enable the electrosurgical device 100 to traverse through a tissue such as an occlusion. In some embodiments, the electrode tip 112 may be formed integrally with the elongate member 112. In other embodiments the electrode tip 112 may be otherwise attached to the elongate member 102 to form a secure connection therewith.

In some embodiments the electrode tip 112 is positioned distal to the heat shield 118. In some embodiments, the electrode tip 112 may be positioned substantially adjacent to the heat shield 118. In one example, the electrode tip 112 may be positioned distal to and adjacent to the distal face of the heat shield 118 as shown in FIGS. 9A-9D. In one example, the heat shield 118 extends substantially radially along a proximal face of the electrode tip 112. In one example, a platinum band may be positioned proximal to the heat shield 118. In another embodiment, the electrode tip 112 is positioned distal to and adjacent a support structure 120 that comprises an annular tubular structure through which core wire 202 is threaded as shown in FIGS. 1A, 1B and 2-4. In some embodiments, the electrode tip 112 may have an outer diameter that is equal or greater than the diameter of the distal components which are adjacent the electrode tip 112, such as the heat shield 118 or a combination of the heat shield 118 and the support structure 120. In other embodiments, the electrode tip 112 and additionally the support structure 120 both have an outer diameter which is equal to or greater than diameter of the heat shield 118. In such embodiments, when the electrode tip 112 is used to create a channel portion through tissue for e.g. an occlusion, by delivering energy through the electrode tip 112, a channel portion is created that is at least as wide as the electrode tip 112 outer diameter. This allows at least the electrosurgical device distal region 104 to be advanced through the occlusion. In still other embodiments, the electrode tip 112 may have a diameter that is less than that of the heat shield and/or the support structure. In some embodiments the electrode tip 112 helps retain the heat shield 118 in position within the device 100. In other words, the electrode tip 112 helps secure the heat shield 118 in place.

In some embodiments, as mentioned above, a support structure 120 is provided distal to the heat shield 118. The support structure 120 provides a distal surface on which the electrode tip 112 may be positioned and/or formed, for example using a welding process. In one specific example, a laser welding process is used and the support structure 120 provides a substantially planar distal face onto which the dome-shaped electrode tip 112 is formed. In one instance of this example, the support structure 120 comprises a material that can withstand the laser welding process and can bond well with the core wire 202. The welding process allows the electrode tip 112 to fuse with the support structure 120 at the interface between the two. Additionally, in some embodiments, the support structure 120 has sufficient mechanical strength to allow it to be machined. Both the core wire 202 and the support structure 120 may be formed from biocompatible materials. In one specific example, the support structure 120 comprises a metal such as Tantalum and the core wire 202 comprises Nitinol. When the Nitinol core wire 202 is laser welded it fuses with the Tantalum support structure 120 at the interface between the two materials. An integral bond is formed at the boundary between the Nitinol electrode tip 112 and the tantalum support structure 120. The Tantalum support structure 120 allows the dome of the Nitinol electrode tip 112 to be formed on a flat surface. In other words, the Tantalum support structure 120 functions as a base to allow the Nitinol electrode tip 112 to be formed onto it.

In some embodiments, the support structure 120 may comprise materials such as tantalum, iridium, gold or stainless steel. In other embodiments, any other suitable material may be used. In one example, the support structure 120 is radiopaque and provides the physician with a visual indication of the location of the electrode tip 112 under imaging. This helps determine the location of electrode tip 112 within the patient's body during use. In one specific example, an annular tubular structure comprising radiopaque tantalum metal is used as the support structure 120. The support structure 120 is threaded onto the distal end of the core wire 202 and the electrode tip 112 is positioned or formed distal to and adjacent to the support structure 120, the support structure 120 being positioned distal to heat shield 118. In some embodiments, the tantalum support structure 120 has an inner diameter of about 0.2 mm to about 0.3 mm, for example about 0.279 mm, an outer diameter of about 0.8 mm to about 0.9 mm, for example about 0.812 mm, and a longitudinal length of about 0.2 mm to about 0.3 mm, for example about 0.254 mm.

In some embodiments, the support structure 120 is electrically conductive and forms a part of the electrode. Thus, the support structure 120 together with the electrode tip 112 can be understood to form the energy delivery component. In one such example, a Nitinol electrode tip 112 is formed on a tantalum support structure 120 that is positioned distal to the heat shield 118. The electrode tip 112 is shaped to provide current density sufficient to generate arcing to create a channel through a region of tissue. Additionally, arcing may be generated at the tantalum support structure 120, for example on its sides or radial edges and at the edges/corners of the support structure 120 at a discontinuity. In some examples, the heat shield 118 is flush with the support structure 120. In other embodiments, the heat shield may not be positioned such that it is flush with the support structure 120 and there may be arcing at the junction/boundary between support structure 120 and the heat shield 118. In other words, if there is a gap at the proximal boundary of the support structure 120, there may be some arcing generated there. In one example, a ceramic filler may be used at this junction to fill the gap. In some applications/uses, for example if there is coagulum formation at the electrode tip 112, then arcing may be generated at the support structure 120. In another example, a substantially thin support structure 120 is used whereby arcing may be generated at the support structure 120. In some embodiments, the arcing observed at the support structure 120, in addition to arcing at the electrode tip 112, may help device 100 to traverse through a relatively large occlusion.

In alternate embodiments the support structure 120 may not be electrically conductive. In some embodiments, the support structure 120 may be flush with and positioned adjacent the electrode tip 112. In some embodiments the support structure 120 and the electrode tip may be attached or secured to one another. In other embodiments, the support structure 120 and the electrode tip 112 may not be attached. As mentioned, in one example, the support structure 120 is electrically conductive and forms an electrode together with electrode tip 112. In another example, the electrode tip 112 substantially forms the electrode. Thus, the electrode tip 112 or the support structure 120 in conjunction with electrode 112 define the energy delivery component of electrosurgical device 100 through which energy can be delivered, for example to a region of tissue within a patient's body.

Various methods may be used to provide an electrode tip 112 that is shaped substantially like a segment of sphere. This may include an electrode tip 112 that is rounded or hemispherical in shape. In some embodiments, the electrode tip 112 that is shaped like a segment of a sphere may be removably attached to the distal end of the electrosurgical device 100. For example, the electrode tip 112 may be a rounded cap electrode and may be removably affixed to the core wire 202 and/or to the support structure 120. Alternatively, in some embodiments, an electrode tip 112 may be coupled/attached directly to a distal end of the elongate member 102 distal to and adjacent to the heat shield 118. As mentioned above, in other embodiments the electrode tip 112 may have surface geometries similar to those shown in FIGS. 9A-9D. In one embodiment, a friction fit may be used such that the electrode tip 112 co-operatively engages with either the elongate member 102 and/or the heat-shield 118. In some embodiments, the electrode tip 112 may be mechanically secured to the elongate member 102 and may abut the heat shield 118 such that it rests against the heat shield 118. In one specific example, the elongate member 102 may comprise a Nitinol wire and the electrode tip 112 may comprise a rounded Nitinol cap and may be attached to the distal tip of wire 102. Alternatively, the electrode tip 112 may comprise a Nitinol 'ball' or sphere. A hole may be created/ground in the ball and the wire 102 may be received within the hole and attached thereto. In some embodiments, the electrode tip 112 may be may be secured to the elongate member 102 and/or heat shield 118 by an adhesive. In one example, the adhesive may comprise an epoxy. In one embodiment, the electrode tip 112 may be attached to wire 102 using a melt-processing method. In some embodiments, the heat shield 118 extends substantially radially along a proximal face of the electrode tip 112. In alternate embodiments, the heat shield 118 extends substantially radially along a proximal face of an annular structure such as support structure 120. In one specific example, the support structure 120 is an annular structure which is electrically conductive and forms a part of the electrode as described hereinabove.

Figure 4:
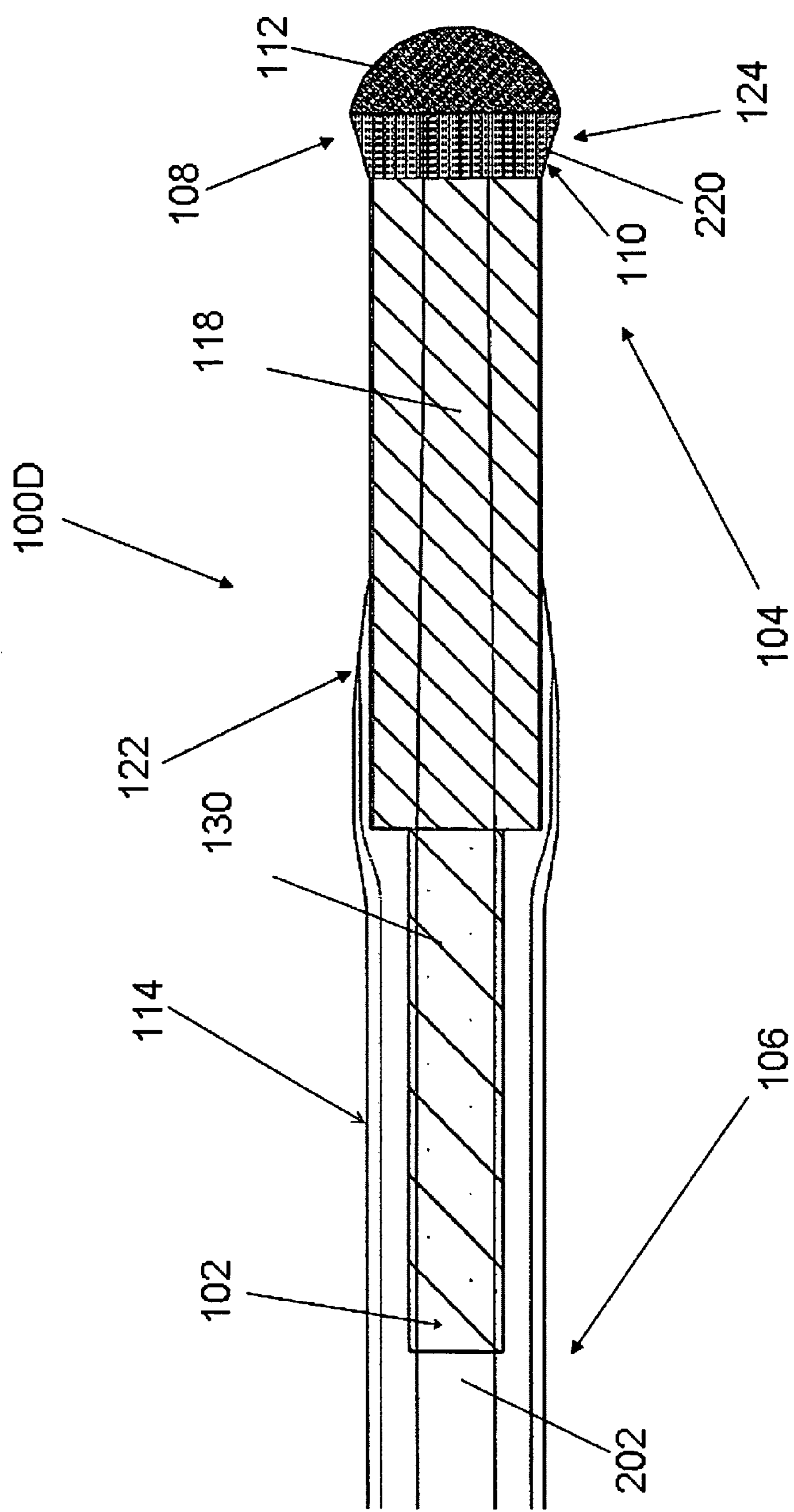
FIG. 4 is an illustration of an electrosurgical device in accordance with an alternate embodiment of the present invention.

In one embodiment of the present invention, a support structure 220 comprises a tapered profile 124, for example as shown in FIG. 4. The support structure 220 may have the properties as discussed above for support structure 120. In one example, the support structure 220 comprises an annular structure that has an outer diameter that gradually tapers from its distal end towards its proximal end as shown in FIG. 4. In one embodiment, the tapered support structure 220 has a distal outer diameter (OD) that matches the outer diameter of the distal electrode tip 112. Furthermore, the tapered support structure 220 has a proximal outer diameter (OD) that matches the outer diameter of the heat shield 118. Thus, a smooth outer profile is created by the tapered support structure 220 which facilitates the advancement of device 100D within tissue within a patient's body. The tapered profile 124 minimizes the risk of tissue snagging or catching at the proximal boundary of the support structure 220. This minimizes the risk of charred tissue getting caught proximal to the electrode tip 112 and the support structure 220. This may further facilitate forward advancement of the device 100D as tissue is targeted by the active electrode tip 112 at the distal tip 108. The tapered profile 124 may also facilitate backward movement or retraction of device 100D during use, for example, within a patient's body (for e.g. within a vessel lumen). In one example, the tapered support structure 220 comprises tantalum. Thus, the tapered profile of tantalum having a distal outer diameter (OD) larger than its proximal OD may allow easier traversal through the occlusion. The distal OD of tantalum may be greater than the device 100D OD along a portion of the device 100D proximal to the support structure.

In some embodiments of the present invention, the electrosurgical device 100 may have an outer diameter (OD) at the distal tip 108 which is greater than the outer diameter (OD) along a portion of the device 100 proximal to the distal tip 108, such as OD of heat shield 118. The wider OD at the distal tip 108 may help facilitate traversal of the electrosurgical device 100 through tissue such as an occlusion. In one example, during use, the larger distal tip OD of device 100 can create a puncture in tissue that is greater than the device OD proximal to the distal tip 108. In other words, the larger distal tip OD allows a channel to be created through tissue, for example an occlusion, that is wider than a segment of device 100 proximal to the distal tip 108. Thus, the wider OD at the distal tip allows the device 100 to traverse easily through the occlusion with minimal risk of hindrance in the device path. This may allow the device 100 to cross with ease through the channel created. The larger distal OD also minimizes the risk of tissue being caught at the junction 122, for e.g. at the over-lap of the insulation layer 114 with the heat shield 118. Furthermore, a portion of the device proximal region 106 may have an outer diameter (OD) that is greater than the distal tip OD. This may allow the device 100 to further dilate the occlusion. In one example, the proximal portion of the device proximal region 106 has an OD that is wider than the distal tip OD. Additionally, in one example, the device proximal region 106 has a tapering profile that increases in diameter towards its proximal portion.

In accordance with an embodiment of the present invention, electrosurgical device 100 allows traversal through occlusions, which may include occlusion harder portions and occlusion softer portions. In some embodiments, the electrosurgical device 100 provides a dome-shaped electrode tip 112 which provides sufficiently intense arcing to facilitate crossing of the device 100 through at least a portion of the harder part of the occlusion.

Figure 8:
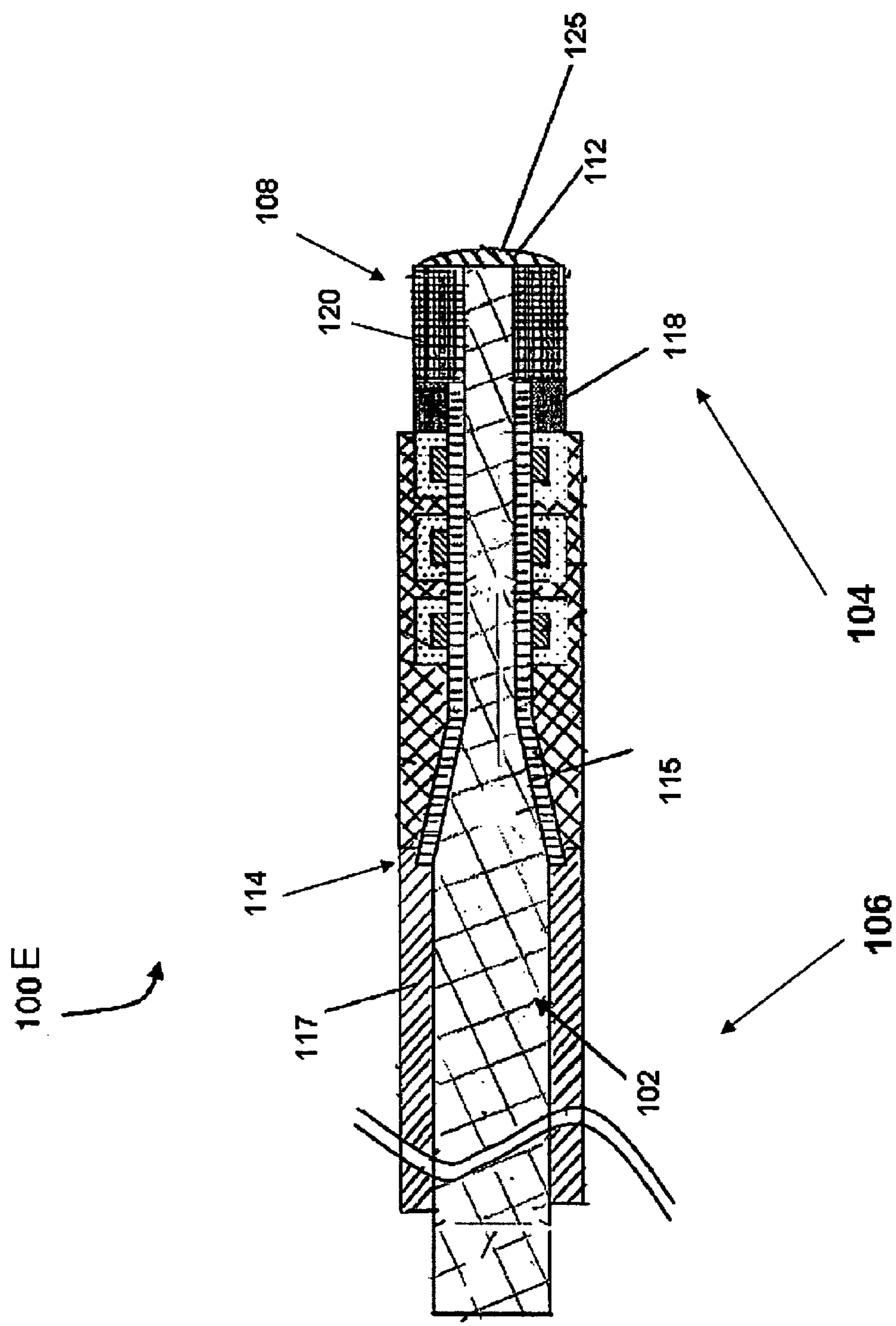
FIG. 8, in a partial side cross-sectional view, illustrates an embodiment of an energy delivery apparatus.

Referring to FIG. 8, the energy delivery apparatus, such as electrosurgical device 100E includes an elongate member, such as a substantially elongated electrical conductor 102, which may be any suitable conductor, such as a wire or a cable made out of a suitable electrically conducting material, such as for example, Nitinol, stainless steel, gold, platinum, titanium, silver or alloys thereof. The electrical conductor 102 is substantially elongated and defines a conductor proximal end and a substantially longitudinally opposed conductor distal end. An electrode tip 112 is electrically coupled to the electrical conductor 102 and located at a predetermined location therealong, for example adjacent to conductor distal end. The electrode tip 112 is provided for delivering electrical energy at a target location.

A proximal region 106 of the electrosurgical device such as a proximal region the electrical conductor 102 having an electrically insulating layer disposed thereon, is positioned in a substantially spaced apart relationship relative to the electrode tip 112.

Spacing apart the proximal region 106 of the electrosurgical device 100 from the electrode tip 112 ensures that any temperature increase caused by the delivery of electrical energy to the target location only minimally affects the device proximal region 106.

In the embodiment of the invention shown in FIG. 8, the proximal region 106 of the electrosurgical device is substantially longitudinally spaced apart from the electrode tip 112. More specifically, the electrode tip 112 is located distally relatively to the device proximal region 106. For example, the electrode tip 112 is located substantially adjacent to the conductor distal end. It is within the scope of the invention to have an electrode tip 112 that is formed integrally by a section of the outermost surface of the electrical conductor 102.

In this embodiment, the electrode tip 112 defines tip distal surface 125 that is shaped substantially similarly to a portion of a sphere, i.e. rounded. This helps to ensure that injuries that may be caused to the body vessels, through movements of the electrode tip 112 through these vessels, are minimized.

In some embodiments of the invention, the energy delivery apparatus 100E includes an electrically insulating material substantially covering the electrical conductor 102, such as for example and non-limitingly, Teflons®, such as polytetrafluoroethylene (PTFE), fluorinated ethylene propylene copolymer (FEP), perfluoroalkoxy (PFA), or ethylene and tetrafluoroethylene copolymer (ETFE, for example Tefzel®), or coatings other than Teflons®, such as polyetheretherketone plastics (PEEK™), parylene, certain ceramics, or polyethylene terpthalate (PET). In some embodiments, the electrically insulating material forms a layer that extends substantially radially outwardly from the electrical conductor 102. The electrically insulating material is described in further details hereinbelow.

In some embodiments of the invention, the energy delivery apparatus 100E further includes a heat shield 118 made out of a substantially thermally insulating material, for example, and non-limitingly, polytetrafluoroethylene (PTFE), which has a thermal conductivity of about 0.3 W/m-K. In this embodiment, the heat shield 118 may have a thickness of at least about 0.025 mm. In other embodiments, the thickness of the heat shield 118 may vary, depending on the thermal conductivity of the material being used. The heat shield 118 is located, at least in part, between the electrode tip 112 and the device proximal region 106. The heat shield 118 is provided for further thermally insulating the device proximal region 106 (having an elongate member 102 with an electrically insulating layer disposed thereon) from the electrode tip 112 and from heat produced by the delivery of electrical energy through the electrode tip 112.

In some embodiments of the invention, the heat shield 118 includes polytetrafluoroethylene (PTFE). The use of PTFE is advantageous as, in addition to having suitable thermal insulation properties, PTFE is also an electrically insulating material (having a dielectric strength of about 24 kV/mm) and, therefore, contributes to the prevention of arcing between the electrode and any metallic material that may be present in the device proximal region 106. In alternate embodiments, other materials, such as for example, Zirconium Oxide, may be used for heat shield 118.

In one embodiment of the invention, the heat shield 118 extends substantially longitudinally from and contacts both the device proximal region 106 and the electrode tip 112. In other words, the heat shield 118 substantially fills a gap between the electrode tip 112 and the device proximal region 106. However, in alternative embodiments of the invention, the heat shield 118 extends substantially longitudinally only from one of the device proximal region 106 and the electrode tip 112 or, alternatively, the heat shield 118 does not contact either one of the device proximal region 106 and the electrode tip 112.

As shown in the drawings, the heat shield 118 is substantially annular and extends substantially radially outwardly away from the electrically insulating material covering the electrical conductor 102. In a very specific embodiment of the invention, the heat shield 118 is substantially annular and has a substantially similar outer diameter as device proximal region 106 and the electrode tip 112. This configuration results in an energy delivery apparatus 100E for which a distal region thereof has a substantially uniform outer diameter, which therefore facilitates navigation of the energy delivery apparatus 100E through body vessels and the creation of channels through occlusions and other biological tissues inside the patient. However, in alternative embodiments of the invention, the heat shield 118, the electrode tip 112 and the device proximal region 106 may all have any other suitable diameters.

In alternative embodiments of the invention, the electrical conductor 102 is made more flexible substantially adjacent the conductor distal end than substantially adjacent the conductor proximal end in any other suitable manner such as, for example, by using different materials for manufacturing the conductor proximal and distal regions. It has been found that a suitable material for manufacturing the actual conductor 102 is Nitinol. Indeed, Nitinol shows super-elastic properties and is therefore particularly suitable for applying relatively large deformations thereto in order to guide the energy delivery apparatus 100E through relatively tortuous paths. Also, since the energy delivery apparatus 100E typically creates channels inside biological tissues through radio frequency perforations, in some embodiments of the invention, the energy delivery apparatus 100E typically does not need to be very rigid.

In some embodiments of the invention, the electrically insulating material 114 is divided into a first electrically insulating material 117 and a second electrically insulating material 115. A first electrically insulating layer 117 made out of the first electrically insulating material substantially covers a first section of the electrical conductor 102. A second electrically insulating layer 115 made out of the second electrically insulating material substantially covers a second section of the electrical conductor 102. The second section is located distally relatively to the first section. Furthermore, the first and second electrically insulating materials may comprise different materials with differing physical properties. For example, in some embodiments, the second electrically insulating material comprises polyimide, while the first electrically insulating material comprises PTFE. This allows for the second electrically insulating layer 115 to be substantially thinner than the first electrically insulating layer 117, while being sufficiently insulative so as to prevent undesired leakage of current. This substantially increases the flexibility of the energy delivery apparatus 100 substantially adjacent the apparatus distal end portion such as distal tip 108. In addition, this provides a material that is substantially more lubricious over the wider section of the energy delivery apparatus 100E so as to facilitate movement of the energy delivery apparatus 100E through body vessels and through channels created within the body.

APPLICATIONS

An embodiment of a treatment method of the present invention may be useful, for example, to penetrate through a material at least partly occluding a vessel of a body of a patient (such as a stenosis) in order to recannalize the vessel. In such an example, the material to be penetrated may comprise a vascular occlusion having regions of various degrees of toughness and calcification. Thus, this particular application may benefit from utilizing electrical energy in conjunction with the mechanical application of pressure in order to penetrate and traverse the occlusion.

Figure 5:
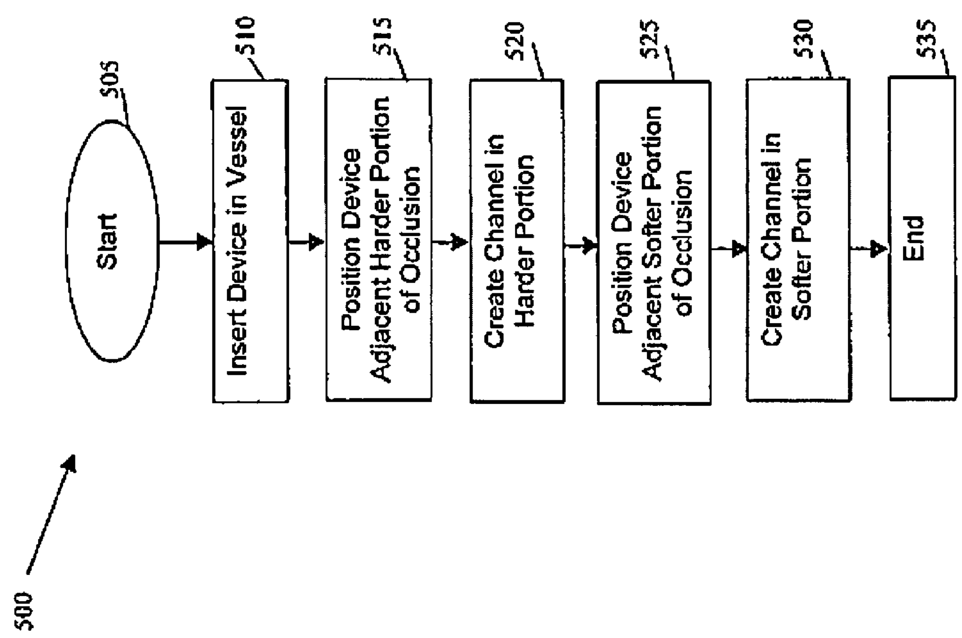
FIG. 5, in a flow chart, illustrates a method for creating a channel in accordance with an embodiment of the present invention.
Figure 6:
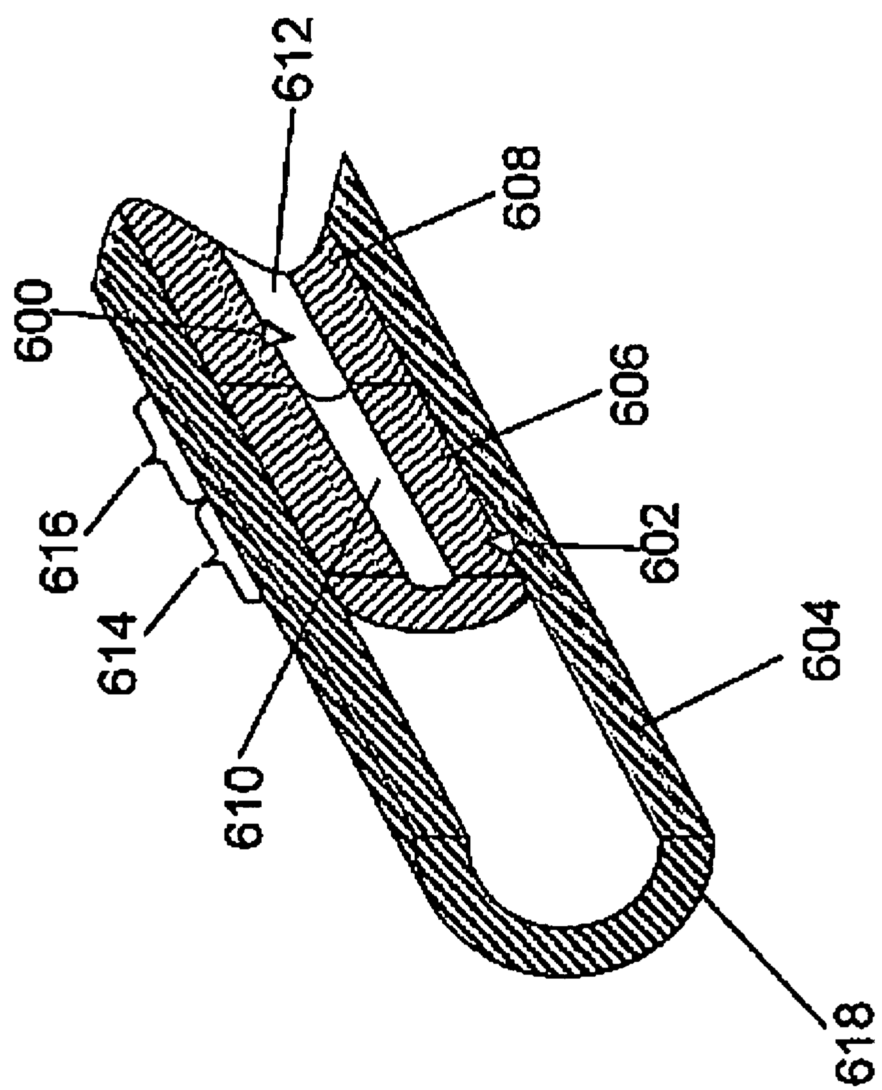
FIG. 6, in a perspective view, illustrates the channel created in an occlusion of a body vessel using the method illustrated in FIG. 5.

Referring to FIGS. 5 and 6, in a more specific example of implementation, the present invention is embodied in a method 500 for creating a channel 600 through an occlusion 602 located in a substantially elongated body vessel 604 of a patient, the occlusion 602 including an occlusion harder portion 606 extending substantially longitudinally relative to the body vessel 602 and an occlusion softer portion 608 extending substantially longitudinally relative to the body vessel 602, the occlusion softer portion 608 being located substantially adjacent to and substantially coaxially with the occlusion harder portion 606. Also, it should be noted that for the purposed of this example and of the appended claims, the term body vessel applied to any suitable body structure defining a lumen, such as for example a blood vessel, a bile duct, an airway, and various tubes and/or ducts associated with the digestive system, the urinary tract and/or the reproductive system, among other possibilities.

For example, it has been found that the proposed method is well suited to the creation of channels through plaque partially or totally occluding a blood vessel. Such occlusions often have harder portions, for example end caps thereof, and located substantially adjacent softer portions, for example the portion of the occlusion located between the end caps.

Also, the person skilled in the art will readily appreciate that the channel 600 is not necessarily a self-supporting channel 600. Therefore, in some embodiments of the invention, the channel 600 is further dilated or receives a stent, or is both dilated and receives a stent, after having been created.

The method 500 uses a channel creating apparatus, such as, for example, an embodiment of the apparatus described hereinabove such as electrosurgical device 100, defining an apparatus distal end portion, such as for example the distal tip 108 described hereinabove, insertable into the body vessel 600. The channel creating apparatus, such as electrosurgical device 100 includes an energy delivery component, such as electrode tip 112 operatively coupled to the apparatus distal end portion for delivering energy proximate the apparatus distal end portion.

The method 500 starts at step 505. Then, at step 510, the apparatus distal end portion is inserted into the body vessel 604.

Afterwards, at step 515, the apparatus distal end portion is positioned proximate the occlusion harder portion 606 and, at step 520, a channel first portion 610 of the channel 600 is created through the occlusion harder section 606. This channel first portion may also be referred to as a channel harder portion. Creating the channel first portion 610 includes delivering the energy into the occlusion harder portion 606.

Subsequently, at step 525, the apparatus distal end portion is positioned proximate the occlusion softer portion 608 and, at step 530, a channel second portion 612 of the channel 600 is created through the occlusion softer portion 608 by pushing the apparatus distal end portion through at least a portion of the occlusion softer portion 608, the channel second portion 612 being created substantially without using the energy delivery component such as electrode tip 112, to deliver energy into the occlusion softer portion 608. This channel second portion may be referred to as a channel softer portion.

For example, the apparatus distal end portion is pushed by applying a substantially longitudinal force to an apparatus proximal portion (for example, the proximal region of the apparatus described hereinabove) longitudinally opposed to the apparatus distal end portion. In another example, the apparatus distal end portion is pushed directly, for example using a motor or any other actuator coupled to the apparatus distal end portion.

It should be noted that while embodiments of the apparatus described hereinabove are usable to perform the method 500, in other embodiments of the invention, any suitable apparatus may be used.

Also, while in the method 500 the channel first portion 610 is created before the channel second portion 612, it is within the scope of the invention to create the channel second portion 612 before the channel first portion 610.

It has been found that the method embodied in FIGS. 5 and 6 leads to a new and unexpected result in which the channel 600 is created relatively easily and relatively safely through both the occlusion harder and softer portions 606 and 608 using the same apparatus, such as electrosurgical device 100. In addition, channel 600 may be created by an apparatus whose mechanical properties are substantially similar to those of standard mechanical guide-wires. Other advantages of the proposed methods have been mentioned hereinabove.

In some embodiments of the invention, the occlusion harder portion 606 has a hardness that is substantially too large to allow pushing the apparatus distal end portion through the occlusion harder portion 606 without delivering the energy into the occlusion harder portion 606. For example, it was found that when the occlusion harder portions 606 has a hardness such that a mechanical pressure of at least about 20 kg/cm$^2$ is required to create a channel thereinto, conventional mechanical guide-wires are typically unusable to create the channel first portion 610. These embodiments of the present invention thus provide a means for traversing an occlusion that standard mechanical guide-wires may be unable to penetrate.

In some embodiments of the invention, step 520 is performed as follows. First, a channel first portion first segment 614 is created through the occlusion harder portion 606 while delivering the energy into the occlusion harder portion 606 and the apparatus distal end portion is advanced through the channel first portion first segment 614. The advancement of the apparatus distal end portion may be simultaneous with or subsequent to the delivery of energy. When the channel first portion first segment 614 has been created, the delivery of energy is stopped. Afterwards, a user of the channel creating apparatus may attempt to push the apparatus distal end portion through the occlusion 602 substantially without delivering energy via the energy delivery component such as electrode tip 112. Upon the apparatus distal end portion being unable to be pushed through the occlusion 602 after having created the channel first portion first segment 614, a channel first portion second segment 616 extending from the channel first portion first segment 614 is created similarly to the channel first portion first segment 614. If required, additional segments of the channel first portion 610 are also similarly created. If the apparatus distal end portion can be pushed through the occlusion 602, the creation of the channel 600 continues as described with respect to the creation of the channel second portion 612.

Therefore, by repeatedly testing for the possibility of creating the channel mechanically after, for example, each energy delivery step, an intended user may lower the risk that the energy delivered may injure tissues that should remain intact, such as for example the vessel wall 618 of the body vessel 604.

In some embodiments of the invention, the energy is delivered for a predetermined amount of time before stopping the delivery of the energy. In other embodiments, the user may decide, during the course of the procedure, on the amount of time during which energy should be delivered. For example, the amount of time during which energy may be delivered may be from about 0.1 seconds to about 5 seconds. In a more specific embodiment of the invention, the amount of time during which energy is delivered for a duration of from about 0.5 second to about 3 seconds. It has been found that these amounts of time allow for the creation of the channel 600 in a reasonable amount of time while reducing the risk of unwanted injuries. During the periods of time described above, the energy may be delivered continuously or as a pulsed waveform.

In other embodiments of the invention, when performing step 520, the intended user assesses continuously, periodically or intermittently the position of the apparatus distal end portion relatively to the occlusion softer portion 608. Upon detection that the apparatus distal end portion is located proximate the occlusion softer portion 608, the delivery of the energy is stopped and the channel second portion 612 is created. For example, the position of the apparatus distal end portion is assessed using a position assessment method selected from the group consisting of an imaging technique, an impedance measurement, a measurement of a force exerted onto the apparatus distal end portion, a measurement of a pressure exerted onto the apparatus distal end portion and a measurement based on ultrasonic signals, among other possibilities.

In these embodiments, assessing the position of the apparatus distal end portion may allow the user to deliver energy to the occlusion 602 over a minimal duration, which again may lower the risk of injuring structures adjacent to the occlusion 602.

In some embodiments, if a user is unable to mechanically advance the apparatus through the occlusion softer portion, the user may choose to deliver energy via the energy delivery component, such as electrode tip 112, or may attempt to re-orient at least a portion of the apparatus. As described hereinabove, such re-orientation may take the form of steering the device in some manner or, alternatively, applying torque to a portion of the device. In some such embodiments, the position of the apparatus may be assessed, as described hereinabove, prior to choosing which course of action to follow.

In some particular situations, an occlusion may comprise another, relatively hard, portion, for example on the opposite end of the first hard portion. In such embodiments, a channel third portion may be created through this hard portion of the occlusion in substantially the same manner as the channel first portion, described hereinabove.

As mentioned hereinabove, the energy delivered may be any suitable energy. For example, the energy may be radiofrequency electromagnetic energy or radiant energy, for example laser light, among other possibilities. When radiofrequency energy is used, it has been found that radiofrequency energy delivered with a power of at least about 5 W at a voltage of at least about 75 Volts (peak-to-peak) produces good channel creation performances while remaining relatively safe for the patient. Also, the use of radiofrequency energy is advantageous as it allows the use of relatively small apparatus distal end portions that are relatively robust, and which therefore are relatively well suited to the creation of the channel second portion 612 using mechanical forces.

In such embodiments, when the distal end portion is re-oriented during the creation of channel 600, energy may be delivered via the energy delivery component, such as electrode tip 112, even in the occlusion softer portion 608, in order to facilitate the re-orientation of the distal end portion.

In some embodiments of the invention, the energy delivery component, such as electrode tip 112 is selectively operable in an energy delivering state and a deactivated state. In the energy delivering state, the energy is delivered proximate the apparatus distal end portion. In the deactivated state, the energy is substantially not delivered proximate the apparatus distal end portion.

When such an energy delivery component, such as electrode tip 112 is used, the method 500 may be performed such that the channel first portion 610 is created through the occlusion harder section 606 by operating the energy delivery component, such as electrode tip 112 in the energy delivering state and delivering the energy into the occlusion harder portion 606. The channel second portion 612 is created through the occlusion softer portion 608 by operating the energy delivery component, such as electrode tip 112 in the deactivated state and pushing the apparatus distal end portion through at least a portion of the occlusion softer portion 608.

An advantageous, but non-limiting, embodiment of the invention using such an energy delivery component, such as electrode tip 112 is one wherein the channel creating apparatus includes a pressure sensor operatively coupled to the apparatus distal end portion for measuring a pressure exerted onto the occlusion by the apparatus distal end portion. Then, in some embodiments of the invention, the method 500 includes operating the energy delivery component, such as electrode tip 112 in the energy delivering state if the measured pressure is substantially above a predetermined pressure and operating the energy delivery component, such as electrode tip 112 in the deactivated state if the measured pressure is substantially below the predetermined pressure. The predetermined pressure is, for example, the pressure at which mechanical penetration is difficult or impossible. The energy delivery is manually switched on or off, or the channel creating apparatus includes a controller for automatically turning the energy delivering apparatus to the deactivated state if the pressure exerted onto the occlusion by the apparatus distal end portion is substantially below the predetermined pressure and turning the energy delivery apparatus to the energy delivering state if the pressure exerted onto the occlusion by the apparatus distal end portion is substantially above a predetermined pressure.

In these embodiments, the activation of energy delivery occurs only if the energy is required to create the channel 600 or a portion thereof. Otherwise, only a mechanical force is used to create the channel 600. This reduces uncertainty and variability in the manner in which the method is performed. Also, by reducing or eliminating the need to repeatedly test for the possibility of creating the channel mechanically, the method may be performed relatively fast with relatively low risks of injuring the patient.

In some embodiments of the invention, if an intended user is unable to push the apparatus distal end portion through the occlusion softer portion 608, the intended user may reorient the apparatus distal end portion within the occlusion softer portion 608 and attempt to push the apparatus distal end portion through the occlusion softer portion 608 substantially without delivering energy via the energy delivery component, such as electrode tip 112. However, in some embodiments of the invention, energy is used to facilitate the reorientation of the apparatus distal end portion.

In any or all of the embodiments described herein, a user may elect to initially use a standard mechanical guide-wire to attempt to penetrate an occlusion. Once a hard portion of the occlusion is encountered, the method 500 as described hereinabove may be employed.

In some embodiments of the invention, the energy delivery apparatus such as electrosurgical device 100 is used such that a channel 600 is created at least partially through the occlusion. This channel may be created by delivering energy through the electrode tip 112 and advancing the apparatus distal end portion such as distal tip 108 into the occlusion 602 simultaneously or after delivering energy.

In some embodiments of the invention, when the intended user of the energy delivery apparatus such as electrosurgical device 100 finds that advancing through the occlusion 602 or any other material becomes relatively difficult, the intended user may retract the apparatus distal end portion and apply electrical energy while a gap exists between the apparatus distal end and the target location. Then, a channel 600 may be created more easily, for example due to the space created between the electrode tip 112 and the occlusion 602. Afterwards, the apparatus distal end portion may then be further advanced through this channel.

In some embodiments of the present invention, as mentioned previously, energy may be delivered from the electrode tip 112 in either a continuous mode or a discontinuous mode. In one example, a continuous mode is used and power is supplied to sustain arcing for a period of about 3 seconds in order to facilitate traversal through an occlusion harder portion 606. In an alternate example, a discontinuous mode is used and power is supplied for a period of about 10 seconds. In one example, power is supplied at a frequency of 1 Hz.

In one embodiment of the method of the present invention, the energy delivery device such as the electrosurgical device 100 is advanced to a target location such as within an elongated vessel 604 within a patient's body. The energy delivery portion such as electrode tip 112 is positioned adjacent an occlusion 602. As outlined above, energy is delivered through the energy delivery portion, such as electrode tip 112, to create arcing allowing device 100 to form a portion of the channel 600 through the occlusion, such as through an occlusion harder portion 606. The electrode tip 112 and the electrosurgical device 100 are mechanically advanced through the occlusion softer portion 608, creating another portion of channel 600. In one embodiment, the electrosurgical device 100 is substantially rigid/stiff along a portion thereof. After a substantial segment of the occlusion 602 has been crossed. A dilation catheter may be advanced over the electrosurgical device 100, in order to further enhance/widen the channel 600. The electrosurgical device 100 is sufficiently stiff along a portion thereof to allow it to function as a rail allowing the dilation catheter to be advanced over it. The dilation catheter having a wider outer diameter along at least a portion thereof, allows the channel 600 within the occlusion 602 to be widened. The dilation catheter may then be withdrawn and a balloon catheter may then be advanced over the electrosurgical device and positioned within the channel 600 created by electrosurgical device 100. The balloon may then be inflated to further dilate or widen the channel 600. The dilation using a balloon catheter may be performed once or multiple times in order to dilate the channel 600.

In an alternate embodiment, the electrosurgical device 100 defines a device distal region 104 having a distal end portion, such as distal tip 108, that has an outer diameter (OD) that is wider than the OD of a proximal portion of the device distal region 104. In one example, the distal end portion of the electrosurgical device has an outer diameter of 5 thou (i.e. 5 thousandths of an inch) at the distal tip 108. The outer diameter of the device distal region 104 then tapers proximally to 25 thou. As mentioned previously, in one example, a proximal portion of the device proximal region 106 has an outer diameter that is wider than the distal tip 108 of the electrosurgical device 100. As the electrosurgical device 100 is advanced through the occlusion 602 the proximal portion of the device proximal region 106 functions to dilate the channel 600. This may help to minimize the step of inserting a dilating catheter over the electrosurgical device 100 in order to further dilate the occlusion. The electrosurgical device 100 thus functions both to traverse through the occlusion (both occlusion harder portions 606 and occlusion softer portions 608) by forming a channel 600 and additionally may function to dilate the channel 600 as it is formed. Thus the step of inserting a dilating catheter may be minimized. A balloon catheter may then be advanced directly over the electrosurgical device 100 and one or more inflations may be used to further wider the channel 600.

Thus, as described hereinabove, in one broad aspect, embodiments of the present invention comprise an electrosurgical device for creating a channel through a region of tissue using energy provided by an electrical energy source, the device defining a device proximal region and a device distal region. An electrically conductive elongate member is provided for receiving the energy from the electrical energy source, the elongate member defining a distal end provided in the device distal region. In addition, an electrical insulation layer surrounds the elongate member along the device proximal region. Furthermore, an electrode tip is electrically coupled to the distal end for delivering the energy, the electrode tip being configured and sized for delivering the energy in a manner such that electrical arcing is generated in the region of tissue in order to create a channel through at least a portion of the region of tissue when the electrode tip is positioned proximate the region of tissue. In this context, "proximate" should be understood to mean that the electrode tip is positioned either substantially adjacent to the tissue or slightly spaced apart from the tissue such that a gap exists between the tissue and the electrode tip. The device is further provided with an electrically insulative thermal shield disposed between the electrode tip and the device proximal region for preventing arcing therebetween during the delivery of the energy and for thermally protecting the device proximal region from heat produced by the delivery of the energy through the electrode tip.

In another broad aspect, a method is described for creating a channel through an occlusion located in a body vessel of a patient, the occlusion including an occlusion harder portion and an occlusion softer portion. The method uses a channel creating apparatus defining an apparatus distal end portion insertable into the body vessel and the channel creating apparatus includes an energy delivery component operatively coupled to the apparatus distal end portion for delivering energy proximate the apparatus distal end portion. The method is accomplished by positioning the apparatus distal end portion proximate the occlusion, creating a harder portion channel through the occlusion harder portion by delivering energy into the occlusion harder portion using the energy delivery component, and creating a softer portion channel through the occlusion softer portion by advancing the apparatus distal end portion through at least a portion of the occlusion softer portion substantially without using the energy delivery component to deliver energy into the occlusion softer portion.

In another broad aspect, embodiments of the present invention comprise a method for creating a channel through an occlusion located in a body vessel of a patient. The method uses a channel creating apparatus defining an apparatus distal end portion insertable into the body vessel, the channel creating apparatus including an energy delivery component operatively coupled to the apparatus distal end portion for delivering energy proximate the apparatus distal end portion. The method is accomplished by: (i) positioning the apparatus distal end portion proximate the occlusion; (ii) testing the occlusion to determine whether the apparatus distal end portion can be advanced through the occlusion (A) by the application of mechanical force or (B) by delivering energy into the occlusion using the energy delivery component; (iii) creating a channel portion through at least a portion of the occlusion by (A) or (B) as determined in step (ii).

In another broad aspect, embodiments of the present invention describe an energy delivery device for creating a channel through a region of tissue using energy provided by an electrical energy source. The device defines a device proximal region and a substantially opposed device distal region, the device proximal region including an electrical insulator at a radial periphery thereof. In other words, the term “device proximal region” as used herein includes the electrical insulator or insulation layer located in that region. Furthermore, the device distal region defines a distal end and the device further includes an energy delivery means for coupling to the energy source, the energy delivery means being positioned at the distal end for delivering energy to the region of tissue. In such an embodiment (i.e. where the electrode tip is at the distal end of the device), the energy delivery means, once positioned, can be understood to itself form the distal end of the complete device. The energy delivery means is shaped to provide a current density sufficient to initiate arcing at the energy delivery means during the delivery of energy allowing the device to create a channel through at least a portion of the region of tissue. The device further includes an electrical and thermal protection means positioned between the device proximal region and the energy delivery means for electrically and thermally protecting the device proximal region from the arcing initiated at the energy delivery means during the delivery of energy.

In another broad aspect, embodiments of the present invention comprise an electrosurgical device for creating a channel through a region of tissue, the device comprising: an elongate member comprising a nickel-titanium alloy operable to be coupled to an energy source and having a distal end; an electrical insulation layer disposed onto the elongate member along a substantial portion thereof including along a device proximal region; an electrode tip coupled to the elongate member distal end for delivering energy to the region of tissue to create a channel through at least a portion of the tissue; an electrically insulative thermal shield disposed between the electrode tip and the device proximal region for preventing arcing therebetween during the delivery of energy and for thermally protecting the device proximal region from heat produced by the delivery of energy through the electrode tip, the thermal shield having a thermal conductivity of greater than about 2 W/m-K; and a tantalum support structure positioned distal to the thermal shield for supporting the electrode tip; wherein the electrode tip is formed by laser welding the elongate member distal end onto the support structure allowing the electrode tip to be laser welded to the support structure and whereby the electrode tip is shaped substantially like a segment of a sphere.

In a yet further aspect, embodiments of a method of creating a channel through an occlusion located in a body vessel of a patient are described. In such embodiments, the method uses an electrosurgical device wherein the electrode tip and the thermal shield define respectively a tip outer diameter and a shield outer diameter, the tip outer diameter being greater than or equal to the shield outer diameter. In addition, the electrosurgical device is insertable into the body vessel and operable to deliver energy through the electrode tip and the electrosurgical device defines a device distal region comprising the electrode tip and the thermal shield. The method is performed by: creating a channel portion through the occlusion by delivering energy through the electrode tip, the channel portion being at least as wide as the tip outer diameter to allow at least the electrosurgical device distal region to be advanced through the occlusion.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An electrosurgical device for creating a channel through a region of tissue using energy provided by an electrical energy source, the electrosurgical device defining a device longitudinal axis, the electrosurgical device comprising:

an electrically conductive elongate member, for receiving the energy from the electrical energy source, the electrically conductive elongate member comprising a core wire;

an energy delivery component provided at a distal end of the electrosurgical device for delivering the energy to the region of tissue, the energy delivery component being electrically coupled to the electrically conductive elongate member, the energy delivery component comprising an electrode tip;

an electrical insulation layer surrounding the electrically conductive elongate member;

an electrically insulative thermal shield disposed between a proximal end of the energy delivery component and the electrical insulation layer for thermally protecting the electrical insulation layer from heat produced by the delivering of the energy through the energy delivery component; and a support structure having a proximal end, wherein the proximal end of the support structure is positioned distally with respect to a distal end of the electrically insulative thermal shield, the support structure defining a substantially planar distal face that is perpendicular to the device longitudinal axis for supporting the electrode tip and for enabling the electrode tip to be formed integrally with the electrically conductive elongate member, the electrode tip being formed onto the substantially planar distal face of the support structure.

2. The electrosurgical device of claim 1, wherein the electrode tip is configured and sized for generating a current density sufficient for initiating arcing at the electrode tip during the delivering of the energy, thereby allowing the electrosurgical device to create the channel through the region of tissue.

3. The electrosurgical device of claim 2, wherein the electrode tip is shaped substantially like a segment of a sphere.

4. The electrosurgical device of claim 2, wherein the support structure is electrically conductive and forms a part of the energy delivery component.

5. The electrosurgical device of claim 4, wherein the electrode tip is fused with the support structure.

6. The electrosurgical device of claim 2, wherein the support structure is radiopaque.

7. The electrosurgical device of claim 1, wherein the electrically conductive core wire comprises a shape memory alloy.

8. The electrosurgical device of claim 7, wherein the shape memory alloy comprises a nickel-titanium alloy.

9. The electrosurgical device of claim 1, further comprising a radiopaque band positioned proximally with respect to the electrically insulative thermal shield.

10. The electrosurgical device of claim 9, wherein the radiopaque band is directly coupled to the electrically conductive core wire adjacent the electrically insulative thermal shield to support the electrically insulative thermal shield on the electrically conductive core wire.

11. The electrosurgical device of claim 1, wherein the electrode tip and the electrically insulative thermal shield define, respectively, a tip outer diameter and a shield outer diameter, the tip outer diameter being greater than or equal to the shield outer diameter.

12. The electrosurgical device of claim 1, wherein a portion of the electrosurgical device is coated with a hydrophilic coating.

* * * * *